United States Patent
Ying et al.

(10) Patent No.: US 8,227,640 B2
(45) Date of Patent: Jul. 24, 2012

(54) PALLADIUM CATALYSTS

(75) Inventors: Jackie Y. Ying, Singapore (SG); Nandanan Erathodiyil, Singapore (SG)

(73) Assignee: Institute of Bioengineering and Nanotechnology, Nanos (SG)

( * ) Notice: Subject to any disclaimer, the term of this patent is extended or adjusted under 35 U.S.C. 154(b) by 36 days.

(21) Appl. No.: 12/532,820

(22) PCT Filed: Mar. 23, 2007

(86) PCT No.: PCT/SG2007/000079
§ 371 (c)(1),
(2), (4) Date: Nov. 9, 2009

(87) PCT Pub. No.: WO2008/118097
PCT Pub. Date: Oct. 2, 2008

(65) Prior Publication Data
US 2010/0113832 A1    May 6, 2010

(51) Int. Cl.
C07C 209/78 (2006.01)
C07C 13/28 (2006.01)
C07C 5/03 (2006.01)
B01J 23/44 (2006.01)
B01J 31/20 (2006.01)
B01J 31/02 (2006.01)

(52) U.S. Cl. .................................................. 564/473

(58) Field of Classification Search .................. None
See application file for complete search history.

(56) References Cited

U.S. PATENT DOCUMENTS

| 6,126,914 A | 10/2000 | Ogasawara et al. |
| 2004/0192542 A1 | 9/2004 | Choudary et al. |
| 2007/0026294 A1* | 2/2007 | Shimazaki et al. ............. 429/44 |

FOREIGN PATENT DOCUMENTS

| CN | 1748860 A | 3/2006 |
| WO | WO 97/43042 A1 | 11/1997 |
| WO | WO 03/064081 A1 | 8/2003 |
| WO | WO 2005/102513 A1 | 11/2005 |
| WO | WO 2005/116140 A1 | 12/2005 |

OTHER PUBLICATIONS

Zhang et al. Adv. Syn. Catal. 2006, 348, 2027-2032.*
Gonzalez-Arellano et al., Adv. Synth. Catal. 2004, 346, 1316-1328.*
SciFinder search histroy.*
Mandal et al. Chemistry of Materials, vol. 16(19), 3714.*
International Search Report from PCT/SG2007/000079, dated May 30, 2007 (3 pages).
Written Opinion from PCT/SG2007/000079, dated May 30, 2007 (4 pages).
International Preliminary Report on Patentability from PCT/SG2007/000079, dated Feb. 26, 2009 (8 pages).

* cited by examiner

Primary Examiner — Melvin C Mayes
Assistant Examiner — Yun Qian
(74) Attorney, Agent, or Firm — Kilpatrick Townsend & Stockton LLP

(57) ABSTRACT

The invention relates to a particulate substance comprising a particulate porous support coupled to a palladium species. The palladium species may comprise palladium nanoclusters. The particulate substance may be used as a catalyst for conducting a carbon-carbon coupling reaction or a reduction.

16 Claims, 8 Drawing Sheets (♦) 10% Pd/C; (▲) 2–3 nm Pd nanoclusters; (■) 4–6 nm Pd nanoclusters

PALLADIUM CATALYSTS

CROSS-REFERENCE TO RELATED APPLICATION

This application is the U.S. National Stage entry under §371 of International Application No. PCT/SG2007/000079, filed Mar. 23, 2007; the contents of which are herein incorporated by reference in their entirety.

TECHNICAL FIELD

The present invention relates to palladium catalysts, processes for making them and methods for using them.

BACKGROUND OF THE INVENTION

The pharmaceutical industry produces 25-100 kg or more of waste for every kg of active pharmaceutical ingredient (API) manufactured. According to a leading practitioner of the industry, the potential waste co-produced with APIs is in the range of 500 million to 2 billion kg/year. Thus, even at a nominal disposal cost of $1/kg, the potential savings associated with waste reduction would be significant compared to pharmaceutical industry's annual sales (US $500 billion in 2003). Most pharmaceuticals syntheses involve the use of homogeneous catalysts, which are difficult to be separated from the products. The resulting metal contamination of the products poses a serious concern in the pharmaceutical industry.

Heterogeneous catalysts may be more stable, cheaper, and easier to be separated from the products. However, their activity and selectivity are often lower than that of homogeneous catalysts. Thus, increasing efforts have been devoted towards developing efficient heterogeneous catalysts. Homogeneous catalysts that have been immobilised on a support would allow for the ease of catalyst recovery and reuse, and would minimize the waste generation and use of toxic chemicals, which is of great interest in the development of green chemical processes.

Palladium-catalyzed reactions have become an important tool in organic synthesis due to their high efficiency, selectivity, and diversity of possible transformations. Palladium-based catalysts have shown remarkable utility in coupling and hydrogenation reactions. However, despite their high activity, the homogeneous palladium-based catalysts suffer from low stability and high costs, which prevent their application in industrial processes. As a heavy metal, palladium is also highly undesirable as a contaminant of pharmaceutical products. To overcome these challenges associated with conventional palladium-based catalysts, heterogeneous and heterogenized catalysts have been developed. Palladium has been supported on materials such as carbon, zeolites, silicates and polymers for catalytic applications. Although these supported palladium catalysts allowed for ease of recovery, palladium leaching remained a significant problem. Additionally, to date polymer- or silica-supported Pd nanoparticles have shown only low chemical efficiency in catalytic applications.

OBJECT OF THE INVENTION

It is an object of the present invention to substantially overcome or at least ameliorate one or more of the above disadvantages.

SUMMARY OF THE INVENTION

In a first aspect of the invention there is provided a particulate substance comprising a particulate porous support coupled to a palladium species. The palladium species may be Pd(0). The palladium species may comprise palladium atoms. The palladium species may comprise palladium clusters, e.g. palladium nanoclusters.

In an embodiment there is provided a particulate substance comprising a particulate porous support coupled to palladium nanoclusters.

The porous support may be a metal oxide support. The metal oxide may be silica. The porous support and the particulate substance may, independently, be mesoporous. The support and the particulate substance may, independently, have a structure in which relatively large pores are connected by relatively small windows. The relatively large pores may have a mean diameter of between about 5 and about 100 nm. The relatively small windows have a mean diameter of between about 2 and about 50 nm. The porous support may be for example mesoporous siliceous foam. The palladium species may be coupled to walls of the pores of the particulate porous support.

The porous support may be complexed to the palladium species. The porous support may be coupled to the palladium species by a coupling group comprising a linking group and a binding group, wherein the binding group is coupled to the palladium species. In some embodiments the binding group does not contain a thiol group. In some embodiments the binding group does not contain sulfur. The binding group may be for example a urea group or a thiourea group.

The palladium nanoclusters may have a mean diameter between about 1 and about 10 nm. The particulate substance may have a mean particle size of between about 1 and about 100 microns. It may have a palladium loading of between about 0.1 and 2 mmol palladium per gram of support.

In a second aspect of the invention there is provided a process for making a particulate substance comprising a particulate porous support coupled to a palladium species, said process comprising:

exposing a functionalised particulate porous support to a solution of a palladium salt, said functionalised particulate porous support comprising binding groups capable of binding the palladium species; and converting the palladium salt to the palladium species so as to generate the particulate substance.

The palladium salt may be a palladium (II) salt. The palladium of the palladium species may be Pd(0). The palladium species may comprise palladium atoms. The palladium species may comprise palladium clusters, e.g. palladium nanoclusters. The porous support may be complexed to the palladium species. The process may comprise the step of coupling the palladium species to the support. This may occur following the conversion of the palladium salt to the palladium species, or may occur as the palladium salt is converted to the palladium species. The step of coupling may comprise complexing the palladium species to the support.

In an embodiment the process comprises:

exposing a functionalised particulate porous support to a solution of a palladium salt, said functionalised particulate porous support comprising binding groups capable of binding palladium nanoclusters; and converting the palladium salt to palladium nanoclusters so as to generate the particulate substance comprising the palladium nanoclusters coupled, e.g. complexed, to the support.

The process may additionally comprise providing the functionalised particulate porous support. This may comprise reacting a particulate porous support to a functionalising reagent to form the functionalised particulate porous support, said functionalising reagent comprising the binding group and an attaching group capable of attaching to the particulate porous support. The binding group may be for example a urea group or a thiourea group. The functionalised particulate porous support may comprise mesoporous siliceous foam.

The invention also provides a particulate substance when made by the process of the second aspect.

In a third aspect of the invention there is provided a method for conducting a Suzuki coupling reaction comprising exposing an aryl halide and an aryl boronic acid to a particulate substance according to the invention.

In a fourth aspect of the invention there is provided a method for conducting a Heck coupling reaction comprising exposing an aryl halide or an aryl halide and an olefin to a particulate substance according to the invention.

In a fifth aspect of the invention there is provided a method for hydrogenating a carbonyl compound comprising exposing the carbonyl compound to a particulate substance according to the invention in the presence of a hydrogen donor species. The hydrogen donor species may be a formate salt, for example ammonium formate, or a mono-, di-, tri- or tetraalkylammonium formate. The hydrogen donor species may be isopropanol or some other suitable alcohol, e.g. 2-butanol. In this case, a base may also be present.

In a sixth aspect of the invention there is provided a method for hydrogenating an olefin comprising exposing the olefin to a particulate substance according to the invention in the presence of hydrogen gas.

In a seventh aspect of the invention there is provided a method for reductive amination of a carbonyl compound comprising exposing the carbonyl compound to a particulate substance according to the invention in the presence of a primary amine and hydrogen gas. The carbonyl compound may be an aldehyde or may be a ketone.

In an eighth aspect of the invention there is provided a method for hydrogenolysis of an epoxide or a diol comprising exposing the epoxide or diol to a particulate substance according to the invention in the presence of a formate salt.

In any of the third to eighth aspects of the invention the catalyst may be been recycled from a previous reaction. In any of these aspects, the method may be regiospecific, stereospecific or both. The reactions may be conducted with high chemical efficiency. The reactions may be conducted with low leaching of palladium from the catalyst.

In a ninth aspect of the invention there is provided use of a particulate substance according to the invention as a catalyst for conducting a carbon-carbon coupling reaction or a reduction.

DETAILED DESCRIPTION OF THE INVENTION

The present invention relates to a particulate substance comprising a particulate porous support coupled to a palladium species, e.g. palladium nanoclusters. Clusters have been defined (http://encyclopedia.thefreedictionary.com/Cluster+chemistry) as follows: "a cluster compound contains a group of two or more metal atoms where direct and substantial metal metal bonding is present" (*Introduction to cluster chemistry* by D. M. P. Mingos, David J Wales 1990 ISBN 0-13-479049-9). F. A. Cotton described them as having a polyhedral cage structure (Cotton and Wilkinson, *Advanced Inorganic Chemistry—A Comprehensive Text*, 3$^{rd}$ Edition, p 31). Nanoclusters therefore may be considered to be clusters having a nanometer scale dimension.

The particulate substance may be prepared by exposing a functionalised particulate porous support to a solution of a palladium salt, said functionalised particulate porous support comprising binding groups capable of binding the palladium species. The particulate substance may be a particulate catalyst. It may be a heterogeneous catalyst. It may be a supported catalyst. It may be a supported palladium catalyst.

The particles of the particulate support, and of the particulate substance, and of the functionalised particulate support, may, independently, be mesoporous. The support and the particulate substance may, independently, have a structure in which relatively large pores (mesopores) are connected by relatively small windows. The relatively large pores may have a mean diameter of between about 5 and about 100. The relatively small windows have a mean diameter of between about 2 and about 50 nm. The porous support may be for example mesocellular siliceous foam. They may be mesocellular siliceous foam according to, or made according to, WO/2006/135339 (Mesocellular foam particles) and/or Han, Y., Lee, S. S., Ying, J. Y. *Chem. Mater.* 2006, 18, 643, the contents of both of which are incorporated herein by reference.

The particles of the particulate support, and of the particulate substance, and of the functionalised particulate support, may, independently, be regular shaped, for example spherical, particles of solid foam. The mean pore size (e.g. cell pore size) may be greater than about 5 nm, or greater than about 10 nm. It may be between about 5 and about 100 nm or between about 5 and 50, 5 and 20, 10 and 100, 50 and 100, 20 and 50, 20 and 30, 20 and 25, 2 and 22, 25 and 30, 27 and 30, 27 and 29, or 10 and 50 nm. The pore size may be about 5, 10, 15, 20, 21, 22, 23, 24, 25, 26, 27, 28, 29, 30, 35, 40, 45, 50, 55, 60, 65, 70, 75, 80, 85, 90, 95 or 100 nm. The particles may have a distribution of different pore sizes. The different pore sizes may be between about 5 and about 100 nm.

The particles of the particulate support, and of the particulate substance, and of the functionalised particulate support, may, independently, have a mean particle diameter of between about 1 and about 100 microns, or between about 5 and 100, 10 and 100, 20 and 100, 50 and 100, 2 and about 50, 20 and 50, 10 and 50, 2 and 40, 1 and 50, 1 and 10, 1 and 5, 1 and 2, 2 and 20, 2 and 10, 3 and 8, 4 and 7, 4 and 6, 5 and 20, 10 and 20, 2 and 10 or 5 and 10 microns, and may have a mean particle diameter of about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90 or 100 microns, or may be less than 1 micron or greater than 100 microns. They may have a narrow particle size distribution. There may be less than about 50% of particles having a particle size more than 10% different from (greater than or less than) the mean particle size, or there may be less than about 45, 40, 35, 30, 25, 20, 15, 10 or 5% of particles having a particle size more than 10% different from the mean particle size, and may be about 1, 2, 3, 4, 5, 10, 15, 20, 25, 30, 35, 40, 45 or 50% of particles having a particle size more than 10% different from the mean particle size. The particles may be spherical, or they may be some other shape, such as ovoid, ellipsoid, cubic, rhomboidal, prismatic, or parallelepiped (for example rectangular parallelepiped).

The ratio of the size of the mesopores and the size of the windows may be between about 10:1 and about 1.5:1, or between about 10:1 and 2:1, 10:1 and 5:1, 5:1 and 1.5:1, 3:1 and 1.5:1, 5:1 and 3:1 or 8:1 and 4:1, and may be about 10:1, 9:1, 8:1, 7:1, 6:1, 5:1, 4.5:1, 4:1, 3.5:1, 3:1, 2.5:1, 2:1 or 1.5:1, or may be some other ratio. The particles may have some other structure. The size of the windows (i.e. window pore size) may be greater than about 2 nm, greater than Stun, or greater than about 10 nm. It may be between about 2 and about 50 nm or between about 2 and 20, 2 and 10, 5 and 50, 5 and 20, 10 and 20, 10 and 15, 10 and 12, 15 and 20, 15 and 18, 15 and 17, 10 and 100, 50 and 100 or 10 and 50 nm. The window size may be about 2, 3, 4, 5, 10, 11, 12, 13, 14, 15, 16, 17, 18, 19, 20, 25, 30, 35, 40, 45 or 50 nm. The particles may have a distribution of different window sizes. The different window sizes may be between about 2 and about 50 nm.

The particles of the particulate support, and of the particulate substance, and of the functionalised particulate support, may, independently, have a pore volume of between about 0.5 and about 5 cm$^3$/g, or between about 0.5 and 4, 0.5 and 3, 0.5 and 2, 1 and 5, 2 and 5, 3 and 5, 1 and 3, 1 and 2, 2 and 3, 1.5 and 2, 1.5 and 1.7, 2 and 2.5, 2.2 and 2.4 or 2 and 2.4, and may have a pore volume about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5 or 5 cm$^3$/g, or more than about 5 cm$^3$/g. The particles may gave a specific surface area of between about 100 and about 1000 m$^2$/g, or between about 100 and 500, 100 and 200, 200 and 1000, 500 and 1000, 200 and 800, 200 and 500, 500 and 800, 500 and 700, 500 and 600, 550 and 600, 550 and 570, 600 and 800, 650 and 750, 670 and 730 or 690 and 710 m$^2$/g, and may have a specific surface area of about 100, 150, 200, 250, 300, 350, 400, 450, 500, 510, 520, 530, 540, 550, 560, 570, 580, 590, 600, 610, 620, 630, 640, 650, 660, 670, 680, 690, 700, 710, 720, 730, 750, 750, 800, 850, 900, 950 or 1000 m$^2$/g, or may have a specific surface area of less than about 100 or greater than about 1000 m$^2$/g.

The porous support may be a metal oxide support. The metal oxide may be silica. It may be alumina. It may be zirconia. It may be titania. It may be a mixed oxide comprising any 2 or 3 of, or all of, aluminium, silicon, titanium and zirconium.

The porous support may be coupled to the palladium species by a coupling group comprising a linking group and a binding group, wherein the binding group is coupled to the species. The binding group may be a non-thiol-containing group. It may be a non-sulfur-containing group. The binding group may comprise for example a urea group, a thiourea group, an amine group, an alcohol group, a thiol group, an imidazole group or some other heterocyclic group or a combination of any two or more of these. The binding group may be based on an ionic liquid, a nitrogen, oxygen and/or sulphur containing polymer or dendrimer. The linking group may have an attaching group which is attached to the porous support. The attaching group may be a silyl group. The binding group may be coupled to the porous support by one linking group, or by two linking groups. The linking group may comprise an alkyl chain. The alkyl chain may be between about 1 and 12 carbon atoms long, or between about 1 and 8, 1 and 6, 1 and 4, 2 and 12, 6 and 12 or 2 and 6 carbon atoms long, e.g. 1, 2, 3, 4, 5, 6, 7, 8, 9, 10, 11 or 12 carbon atoms long. Suitable coupling groups include —Si(CH$_2$)$_3$NHCONH$_2$, —Si(CH$_2$)$_3$NHCSNH$_2$, —Si(CH$_2$)$_3$NHCONH(CH$_2$)$_3$Si— and —Si(CH$_2$)$_3$NHCSNH(CH$_2$)$_3$Si—.

The particulate substance may be hydrophilic. It may be hydrophobic. Each of the porous substrate and the functionalised porous substrate may, independently, be hydrophilic, or each may, independently, be hydrophobic. The hydrophobicity of the particulate substance may be adjusted in order to improve or optimise its performance, and/or to improve its compatibility with organic solvents. The particulate substance may have hydrophobic groups on its pore surfaces. The hydrophobic groups may be for example trialkylsilyl groups, dialkylsilanediyl groups or some other hydrophobic group. Suitable groups include trimethylsilyl, triethylsilyl and triphenylsilyl. The particulate substance may have no hydrophobic groups on its pore surfaces other than the coupling group. It may have silanol groups on its pore surfaces.

The palladium species may be a catalytically active palladium species. It may be a high efficiency catalytically active palladium species. It may be catalytically active for hydrogenation or hydrogenolysis. It may be catalytically active for a Suzuki or a Heck reaction, or for a hydrogenation, hydrogenolysis or other reductive reaction. The palladium species may be a Pd(0) species. It may comprise palladium atoms, or it may comprise palladium clusters, e.g. palladium nanoclusters or it may comprise both palladium atoms and palladium clusters. The palladium nanoclusters may be catalytically active nanoclusters. The palladium nanoclusters may have a mean diameter between about 1 and about 10 nm, or between about 1 and 5, 1 and 2, 2 and 10, 5 and 10, 2 and 8, 2 and 6, 2 and 3 or 4 and 6 nm, e.g. about 1, 2, 3, 4, 5, 6, 7, 8, 9 or 10 nm. The nanoclusters may be dispersed uniformly on the support. They may be dispersed uniformly on the pore surfaces of the support. The palladium nanoclusters may be spherical. They may be pseudospherical. They may be approximately spherical. They may be polyhedral. They may be coupled to the binding group by coordination, i.e. they may be coordinated to the binding group. The binding group may be a ligand for the palladium species. The particulate substance may have a palladium loading of between about 0.1 and about 2 mmol palladium per gram of support, or about 0.1 to 1, 0.1 to 0.5, 0.1 to 0.2, 0.2 to 2, 0.5 to 2, 1 to 2, 0.5 to 1.5 or 0.5 to 1 mmol palladium per gram of support, e.g. about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95 or 2 mmol palladium per gram of support.

Thus in one embodiment there is provided a particulate substance comprising particulate porous silica coupled to palladium nanoclusters.

In another embodiment there is provided a particulate substance comprising particulate MCF coupled to palladium nanoclusters.

In another embodiment there is provided a particulate substance comprising particulate MCF coupled to palladium nanoclusters by means of binding groups which are capable of binding the palladium nanoclusters.

In another embodiment there is provided a particulate substance comprising particulate MCF coupled to palladium nanoclusters by means of binding groups which contain urea groups.

In another embodiment there is provided a particulate substance comprising particulate MCF coupled to palladium nanoclusters by means of binding groups which contain thiourea groups.

The present invention also provides a process for making a particulate substance comprising a particulate porous support coupled to a palladium species, said process comprising:
  exposing a functionalised particulate porous support to a solution of a palladium salt, said functionalised particulate porous support comprising binding groups capable of binding the palladium species; and
  converting the palladium salt to the palladium species so as to generate the particulate substance.

The step of converting the palladium salt to the palladium species may comprise reducing the palladium salt. The palladium salt may be a Pd(II) salt. The step of converting may therefore comprise reducing Pd(II) to Pd(0). The reducing may comprise exposing the palladium salt to a reducing agent. It may comprise exposing it to an oxidisable species. The reducing agent (or oxidisable species) may be an alcohol, preferably a primary or secondary alcohol, e.g. methanol.

The functionalised particulate porous support may comprise the particulate porous support, described above, having a coupling group, as also described above, coupled to the surface of the pores thereof. The loading of coupling group on the particulate porous support may be between about 0.5 and about 5 mmol per gram of functionalised particulate porous support, or about 0.5 to 2, 0.5 to 1, 1 to 5, 2 to 5, 1 to 3 or 1.5 to 2.5 mmol/g, e.g. about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 3, 3.5, 4, 4.5 or 5 mmol/g. The palladium salt may be a Pd(II) salt, e.g. palladium chloride, palladium acetate or some other suitable salt. The solution of the palladium salt may be a solution in an organic solvent. The organic solvent may be anhydrous. It may be for example dichloromethane, chloroform, dibromomethane, bromoform, carbon tetrachloride, toluene, acetone, chlorobenzene methanol, ethanol, isopropanol, ethylacetate or some other suitable solvent. The exposing may comprise adding the palladium salt, or a solution thereof, to a suspension of the functionalised particulate support in a carrier. The carrier may be a solvent for the palladium salt. It may be a non-solvent for the palladium salt. The exposing may be for sufficient time and at sufficient temperature for conversion of the palladium salt to the palladium species, e.g. for formation of palladium clusters on the functionalised particulate support. It may be for between about 6 and about 60 hours, or about 6 to 48, 6 to 36, 6 to 24, 6 to 18, 12 to 60, 12 to 36, 24 to 60, 48 to 60, 18 to 30 or 20 to 25 hours, e.g. about 6, 9, 12, 15, 18, 21, 24, 27, 30, 33, 36, 39, 42, 45, 48, 51, 54, 57 or 60 hours. It may be at a temperature of between about 40 and about 100° C., or about 40 to 80, 40 to 60, 60 to 100, 80 to 100, 50 to 80 or 50 to 70° C., e.g. about 40, 50, 60, 70, 80, 90 or 100° C. The temperature may be less than or equal to the boiling point of the carrier. It may be conducted under anhydrous conditions. It may be conducted under anoxic conditions. It may be conducted, for example, under nitrogen, argon, helium, carbon dioxide, or may be under degassed conditions. During the reaction the reaction mixture may be stirred or otherwise agitated, or it may be unstirred and unagitated.

Thus in one embodiment the process comprises exposing, optionally heating, a suspension of the functionalised particulate porous support in an anhydrous carrier to a solution of a palladium (II) salt in an anhydrous solvent, thereby forming a particulate substance comprising a particulate porous support coupled to palladium nanoclusters, said functionalised particulate porous support comprising binding groups capable of binding the palladium nanoclusters.

In some embodiments, the particulate substance has hydrophobic groups on its pore surfaces. In order to achieve this, the porous support from which the particulate substance is made may have hydrophobic groups on its pore surfaces. Thus the process may comprise hydrophobing the particulate substance or the porous support. It may comprise attaching hydrophobic groups to the pore surfaces of the particulate substance or of the porous support. It may comprise adding, for example, trialkylsilyl groups, dialkylsilyl groups or some other hydrophobic group to the pore surfaces of the particulate substance or of the porous support. This may involve treating the porous support with a hydrophobing agent. The hydrophobing agent may comprise for example $(R_3Si)_2O$, $(R_3Si)_2NH$, $R_3SiX$, $R_2SiX_2$ or $RSiX_3$, where R is an alkyl (e.g. methyl, ethyl, propyl etc.) or an aryl (e.g. phenyl) group and X is a suitable leaving group such as Cl, Br, OAc etc. Commonly used hydrophobing agents include hexamethyldisilazane, trimethylsilyl chloride and dichlorodimethylsilane. The step of hydrophobing may be conducted before attaching the coupling group to form the fuctionalised porous support. It may be conducted after attaching the coupling group to form the fuctionalised porous support but before formation of the palladium microclusters. It may be conducted after formation of the palladium species.

Following the formation of the palladium species, the particulate substance may be separated from the reaction mixture. The separating may comprise filtering, centrifuging, settling, decanting or any combination thereof. The particulate substance may then be washed. The washing may be with an organic solvent, e.g. the solvent used for dissolving the palladium salt, or the carrier used to suspend the functionalised particulate porous support, or some other solvent. It may be washed once. It may be washed more than once, in which the washings may use the same solvent or different solvents. The particulate substance may be dried. The drying may comprise heating, passing a gas over and/or through the particulate substance, applying a vacuum or partial vacuum to the particulate substance, or some combination of these.

Thus in another embodiment the process comprises:
  i) exposing a suspension of the functionalised particulate porous support in a carrier to a solution of a palladium (II) salt in a solvent for sufficient time and at a sufficient temperature to form a particulate substance comprising a particulate porous support coupled to palladium nanoclusters,
  ii) separating the particulate substance
  iii) washing the particulate substance, and
  iv) drying the particulate substance,
said functionalised particulate porous support comprising binding groups capable of binding the palladium nanoclusters.

The process may additionally comprise providing the functionalised particulate porous support. This may comprise reacting a particulate porous support to a functionalising reagent to form the functionalised particulate porous support, said functionalising reagent comprising the binding group and an attaching group capable of attaching to the particulate porous support. The binding group may be for example a urea group or a thiourea group. The functionalised particulate porous support may comprise mesoporous siliceous foam.

As described earlier, a suitable particulate porous support is mesocellular siliceous foam, which may be prepared by known methods. The support may be dried before use. The drying may comprise heating for a suitable time at a suitable temperature. The time may be for example between about 6 and about 60 hours, or about 6 to 48, 6 to 36, 6 to 24, 6 to 18, 12 to 60, 12 to 36, 24 to 60, 48 to 60, 18 to 30 or 20 to 25 hours, e.g. about 6, 9, 12, 15, 18, 21, 24, 27, 30, 33, 36, 39, 42, 45, 48, 51, 54, 57 or 60 hours. The temperature may be between about 70 and about 200° C., or about 70 to 150, 70 to 100, 100 to 200, 150 to 200, 100 to 150, 80 to 120 or 90 to 110° C., e.g. about 70, 80, 90, 100, 110, 120, 130, 140, 150, 160, 170, 180, 190 or 200° C. The support may then be cooled in a dry environment, e.g. in dry argon, dry helium, dry nitrogen, dry carbon dioxide etc. Alternatively or additionally the support may be dried by exposure to (or washing with) a dry solvent, e.g. anhydrous ether, anhydrous THF, anhydrous toluene or some other anhydrous solvent. Methods for rendering these solvents anhydrous are well known in the literature.

The support may then be combined with a carrier to form a suspension. The carrier may be an organic solvent, as described earlier. The functionalising reagent, optionally in solution, may then be added to the suspension. The functionalising reagent may be added at a ratio of between about 1 and 5 mmol per gram of support, however this ratio may depend on the nature of the support. The ratio may be between about 1 and 4, 1 and 3, 2 and 5, 3 and 5, 2 and 4 or 2 and 3 mmol per gram of support, e.g. about 1, 1.5, 2, 2.1, 2.2, 2.3, 2.4, 2.5, 3, 3.4, 4, 4.5 or 5 mmol/g. The functionalising reagent should be such that the functionalised particulate porous support comprises binding groups capable of binding or coupling to the palladium species. Suitable functionalising reagents include $(RO)_3Si(CH_2)_3NHCONH_2$, $(RO)_3Si(CH_2)_3NHCSNH_2$, $(RO)_3Si(CH_2)_3NHCONH(CH_2)_3Si(OR)_3$ and $(RO)_3Si(CH_2)_3NHCSNH(CH_2)_3Si(OR)_3$, where R is an alkyl group, e.g. a C1 to C6 alkyl group (e.g. methyl, ethyl, propyl, isopropyl etc.) or an aryl group (e.g. phenyl), however other suitable reagents will be readily apparent to those skilled in the art. Reaction of the support with the reagent in the suspension may be at a temperature and for a time sufficient to react the reagent with the support. The reagent may react with functional groups (e.g. Si—OH groups) on the surfaces of the pores of the support. The time may be for example between about 6 and about 60 hours, or about 6 to 48, 6 to 36, 6 to 24, 6 to 18, 12 to 60, 12 to 36, 24 to 60, 48 to 60, 18 to 30 or 20 to 25 hours, e.g. about 6, 9, 12, 15, 18, 21, 24, 27, 30, 33, 36, 39, 42, 45, 48, 51, 54, 57 or 60 hours. The temperature may be between about 40 and about 100° C., or about 40 to 80, 40 to 60, 60 to 100, 80 to 100, 50 to 80 or 50 to 70° C., e.g. about 40, 50, 60, 70, 80, 90 or 100° C. The reaction may be conducted under anhydrous conditions. It may be conducted under anoxic conditions. It may be conducted, for example, under nitrogen, argon, helium, carbon dioxide, or may be under degassed conditions. During the reaction the reaction mixture may be stirred or otherwise agitated, or it may be unstirred and unagitated.

Following the reaction of the functionalising reagent with the support, the resulting functionalised support may be separated from the reaction mixture. The separating may comprise filtering, centrifuging, settling, decanting or any combination thereof. The functionalised support may then be washed. The washing may be with an organic solvent. It may be washed once. It may be washed more than once, in which the washings may use the same solvent or different solvents. Suitable solvents include toluene, ethanol, acetone, dichloromethane, chloroform, carbon tetrachloride, acetone or other organic solvents, or combinations thereof. The functionalised support may be dried. The drying may comprise heating, passing a gas over and/or through the functionalised support, applying a vacuum or partial vacuum to the functionalised support, or some combination of these. Prior to the drying, the functionalised support may be heated in a solvent, e.g. an alcohol such as ethanol, isopropanol etc. This step may serve to wash the support, in order to remove impurities. The heating may be for between about 6 and about 60 hours, or about 6 to 48, 6 to 36, 6 to 24, 6 to 18, 12 to 60, 12 to 36, 24 to 60, 48 to 60, 18 to 30 or 20 to 25 hours, e.g. about 6, 9, 12, 15, 18, 21, 24, 27, 30, 33, 36, 39, 42, 45, 48, 51, 54, 57 or 60 hours. It may be at a temperature of between about 40 and about 80° C., or 40 to 60, 60 to 80 or 50 to 70° C., e.g. about 40, 50, 60, 70 or 80° C.

Thus in a further embodiment the process of the invention comprises:
  i) exposing a suspension of a particulate porous support to a functionalising reagent to form a functionalised particulate porous support; and
  ii) exposing a suspension of the functionalised particulate porous support to a solution of a palladium (II) salt in a solvent for sufficient time and at a sufficient temperature to form a particulate substance comprising a particulate porous support coupled to palladium nanoclusters;
said functionalising reagent being such that the functionalised particulate porous support comprises binding groups capable of binding the palladium nanoclusters.

In another embodiment the process comprises:
  i) exposing a suspension of a particulate porous support to a functionalising reagent to form a functionalised particulate porous support;
  ii) exposing a suspension of the functionalised particulate porous support to a solution of a palladium (II) salt in a solvent for sufficient time and at a sufficient temperature to form a particulate substance comprising a particulate porous support coupled to palladium nanoclusters;
  iii) separating the particulate substance;
  iv) washing the particulate substance; and
  v) drying the particulate substance;
said functionalising reagent being such that the functionalised particulate porous support comprises binding groups capable of binding the palladium nanoclusters.

In another embodiment the process comprises:
  i) exposing a suspension of mesocellular siliceous foam (MCF) to a functionalising reagent to form functionalised MCF;
  ii) exposing a suspension of the functionalised MCF to a solution of a palladium (II) acetate for sufficient time and at a sufficient temperature to form a particulate substance comprising MCF coupled to palladium nanoclusters;
  iii) separating the particulate substance
  iv) washing the particulate substance, and
  v) drying the particulate substance;
said functionalising reagent being such that the functionalised MCF comprises binding groups capable of binding the palladium nanoclusters.

The particulate substance of the invention may be used as catalysts. They may catalyse reactions that are capable of being catalysed by the palladium species, e.g. by palladium nanoclusters. Thus the invention also provides methods for using the particulate substance of the invention for catalysing various chemical reactions. The catalysing may be conducted with high chemical efficiency, as described below for individual reactions. The Suitable reactions that may be catalysed by these particulate substances include carbon-carbon bond formations and hydrogenations. Examples include a Suzuki coupling reaction of an aryl halide and an aryl boronic acid, a Heck coupling reaction of an aryl halide and an olefin, transfer hydrogenation of a carbonyl compound, hydrogenation of an olefin, reductive amination, hydrogenolysis etc. Typical reaction conditions for these reactions when catalysed by the particulate substance of the present invention (referred to below as "catalyst") are as follows:

Suzuki reaction: aryl halide (e.g. bromide or iodide), aryl boronic acid and catalyst are heated in a solvent for sufficient time to achieve reaction. The molar ratio of aryl halide to aryl boronic acid may be between about 1:1 and about 1:2 based on functional groups. Thus if an aryl dihalide is reacted with an aryl monoboronic acid, a molar ratio of 1:1 would require 1 mole of aryl dihalide and 2 moles of aryl monoboronic. The molar ratio of aryl halide to aryl boronic acid may be between about 1:1 and 1:1.5, 1:1.5 and 1:2 or 1:1.1 and 1:1.3, e.g. about 1:1, 1:1.05, 1:1.1, 1:1.15, 1:1.2, 1:1.25, 1:1.3, 1.35, 1:1.4, 1:1.45 or 1:1.5. Catalyst may be present at a level of between about 0.1 and about 10 mol % relative to aryl halide. In this context 1 mol % of catalyst relative to aryl halide is defined as 1 mole of palladium species in the catalyst per 100 mol halide in the aryl halide. The catalyst may be present at a level of about 0.1 to 5, 0.1 to 2, 0.1 to 1, 0.1 to 0.5, 0.5 to 10. 1 to 10, 2 to 10, 5 to 10, 0.5 to 5, 0.5 to 2 or 1 to 5 mol %, e.g. about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9 or 10 mol %. The reaction mixture may also comprise a base, e.g. a carbonate, e.g. sodium carbonate. This may be at a molar ratio to the aryl halide of between about 1:1 and about 2:1, or about 1:1 to 1.5:1, 1.5:1 to 2:1 or 1.3:1 to 1.7:1, e.g. about 1:1, 1.1:1, 1.2:1, 1.3:1, 1.4:1, 1.5:1, 1.6:1, 1.7:1, 1.8:1, 1.9:1 or 2:1. The reaction may be conducted in a solvent, e.g. an aqueous solvent. The solvent may be an alcohol/water mix, e.g. ethanol water. It may be conducted in an inert atmosphere, e.g. argon, nitrogen, helium, carbon dioxide or a mixture of any two or more thereof. The reaction may be conducted at a temperature of between about 40 and about 100° C., or about 40 to 80, 40 to 60, 60 to 100, 80 to 100, 50 to 80 or 70 to 90° C., e.g. about 40, 50, 60, 70, 80, 90 or 100° C. The reaction time may be between about 6 and about 60 hours, or about 6 to 48, 6 to 36, 6 to 24, 6 to 18, 12 to 60, 12 to 36, 24 to 60, 48 to 60, 18 to 30 or 20 to 25 hours, e.g. about 6, 9, 12, 15, 18, 21, 24, 27, 30, 33, 36, 39, 42, 45, 48, 51, 54, 57 or 60 hours. The reaction may be conducted under microwave conditions. In this case the reaction time may be shortened. Under microwave conditions the reaction time may be between about 1 and about 60 minutes, or about 1 to 30, 1 to 20, 1 to 10, 1 to 5, 5 to 30, 10 to 30, 20 to 30, 5 to 20 or 5 to 15 minutes, e.g. about 5, 10, 15, 20, 25, 30, 40, 50 or 60 minutes. A suitable microwave source is a CEM Discover® microwave reactor system. The intensity of the microwave radiation may be from about 0 to about 100 W, or about 1 to 100, 5 to 100, 10 to 100, 20 to 100, 50 to 100, 0 to 50, 0 to 20, 0 to 10, 0 to 5, 0 to 2, 1 to 50, 1 to 20, 1 to 10, 1 to 5, 1 to 2, 5 to 50, 10 to 50, 20 to 50, 5 to 20, 10 to 20 or 5 to 10, e.g. about 0, 1, 2, 3, 4, 5, 6, 7, 8, 9, 10, 15, 20, 25, 30, 35, 40, 45, 50, 55, 60, 65, 70, 75, 80, 85, 90, 95 or 100 W. The yield from this reaction is commonly high, and may be between about 80 and about 100% based on aryl halide, or about 80 to 95, 80 to 90, 90 to 100, 95 to 100 or 90 to 95%, e.g. about 80, 81, 82, 83, 84, 85, 86, 87, 88, 89, 90, 91, 92, 93, 94, 95, 96, 97, 98, 99 or 100%. The catalyst may be reused for subsequent reactions.

Heck reaction: an aryl halide (e.g. bromide or iodide) or an aryl triflate (i.e. trifluoromethanesulfonate), an olefin, a base and the catalyst are heated in a solvent for sufficient time to achieve reaction. The olefin may be an activated olefin. It may be an electron deficient olefin. It may be an α,β-unsaturated acid, ester or amide. The molar ratio of aryl halide (or aryl triflate) to olefin may be between about 1:1 and about 1:2 based on functional groups. The molar ratio of aryl halide to aryl boronic acid may be between about 1:1 and 1:1.5, 1:1.5 and 1:2 or 1:1.1 and 1:1.3, e.g. about 1:1, 1:1.05, 1:1.1, 1:1.15, 1:1.2, 1:1.25, 1:1.3, 1.35, 1:1.4, 1:1.45 or 1:1.5. Catalyst may be present at a level of between about 0.1 and about 10 mol % relative to aryl halide. The catalyst may be present at a level of about 0.1 to 5, 0.1 to 2, 0.1 to 1, 0.1 to 0.5, 0.5 to 10. 1 to 10, 2 to 10, 5 to 10, 0.5 to 5, 0.5 to 2 or 1 to 5 mol %, e.g. about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9 or 10 mol %. The base may be an amine. It may be a tertiary amine. It may be a trialkylamine. It may be for example triethylamine, tripropylamine or some other suitable base. It may be present in a molar ratio to the aryl halide or triflate of between about 1:1 and about 1:3, or about 1:1 to 1:2, 1:2 to 1:3 or 1:1.5 to 1:1:2.5, e.g. about 1:1, 1:1.5, 1:2, 1:2.5 or 1:3. The reaction may be conducted in a solvent, e.g. an organic solvent. The solvent may be for example toluene, xylene, benzene, chloroform, carbon tetrachloride or some other suitable solvent. The reaction may be conducted in an inert atmosphere, e.g. argon, nitrogen, helium, carbon dioxide or a mixture of any two or more thereof. It may be conducted at a temperature of between 70 and about 150° C., provided that the temperature does not exceed the boiling point of the solvent. The temperature may be between about 70 and 100, 100 and 150, 80 and 130 or 90 and 110° C., e.g. about 70, 80, 90, 100, 110, 120, 130, 140 or 150°. The reaction should be conducted for sufficient time to obtain the desired conversion. The reaction time may be between about 6 and about 60 hours, or about 6 to 48, 6 to 36, 6 to 24, 6 to 18, 12 to 60, 12 to 36, 24 to 60, 48 to 60, 18 to 30 or 20 to 25 hours, e.g. about 6, 9, 12, 15, 18, 21, 24, 27, 30, 33, 36, 39, 42, 45, 48, 51, 54, 57 or 60 hours. As described above for the Suzuki reaction, this reaction may also be accelerated by use of microwave irradiation, using the conditions described earlier. The yield from this reaction is commonly high, and may be between about 80 and about 100% based on aryl halide, or about 80 to 95, 80 to 90, 90 to 100, 95 to 100 or 90 to 95%, e.g. about 80, 81, 82, 83, 84, 85, 86, 87, 88, 89, 90, 91, 92, 93, 94, 95, 96, 97, 98, 99 or 100%. The catalyst may be reused for subsequent reactions.

Transfer hydrogenation: a carbonyl compound and a hydrogen donor species, e.g. a formate salt, are reacted in the presence of the catalyst to form an alcohol. The carbonyl compound may be a ketone. It may be an aryl ketone. It may be an aryl alkyl ketone. The aryl group may be a heteroaryl group, a metallocenyl group or some other type of aromatic group. The alkyl may be straight chain, branched chain, cyclic or some combination of these. It may be for example methyl, ethyl, propyl, isopropyl or some other alkyl group. The aryl group and the alkyl group may, independently, be substituted or unsubstituted. The formate salt may be an amine formate salt. The amine may be ammonia (whereby the amine salt is ammonium formate) or may be an alkyl, dialkyl or trialkyl ammonium salt. Suitable formate salts include triethylammonium and trimethylammonium formate. The formate salt may be generated in situ or separately, by reaction of formic acid with the amine (or ammonia) in a molar ratio of about 1:1. The hydrogen donor species may alternatively be an alcohol or some other hydrogen donor. In this case the reaction may be conducted under basic conditions, e.g. in the presence of a solid hydroxide salt. Catalyst may be present at a level of between about 1 and about 50 mol % relative to carbonyl compound. The catalyst may be present at a level of about 1 to 25, 1 to 10, 1 to 5, 5 to 50, 10 to 50, 25 to 50, 5 to 20 or 5 to 15 mol %, e.g. about 1, 2, 3, 4, 5, 6, 7, 8, 9, 10, 11, 12, 13, 14, 15, 20, 25, 30, 35, 40, 45 or 50 mol %. The reaction may be conducted at room temperature, or at some other convenient temperature, e.g. between about 15 and about 30° C., or between about 15 and 25, 15 and 20, 20 and 30 or 15 and 25° C., e.g. about 15, 20, 25 or 30° C. The ratio of formate salt to carbonyl compound may be between about 2:1 and about 10:1, e.g. about 2:1 to 5:1, 5:1 and 10:1 or 3:1 and 7:1, e.g. about 2:1, 3:1, 4:1, 5:1, 6:1, 7:1, 8:1, 9:1 or 10:1. The reaction may be conducted for sufficient time to achieve a desired conversion. Typical reaction times are between about 1 and about 36 hours. Commonly reaction times are shorter when using ammonium formate than when using an alkylammonium formate. The reaction time may be about 1 to 24, 1 to 12, 1 to 6, 1 to 3, 6 to 12, 12 to 18, 18 to 24, 24 to 36, 6 to 36, 12 to 36 or 18 to 36 hours, e.g. about 1, 2, 3, 4, 5, 6, 9, 12, 15, 18, 21, 24, 27, 30, 33 or 36 hours. The reaction may be conducted under microwave conditions. In this case the reaction time may be shortened. Under microwave conditions the reaction time may be between about 1 and about 30 minutes, or about 1 to 20, 1 to 10, 1 to 5, 5 to 30, 10 to 30, to 30, 5 to 20 or 5 to 15 minutes, e.g. about 5, 10, 15, 20, 25 or 30 minutes. As described above for the Suzuki reaction, this reaction may also be accelerated by use of microwave irradiation, using the conditions described earlier. The yield from this reaction is commonly high, and may be between about 80 and about 100% based on aryl halide, or about 80 to 95, 80 to 90, 90 to 100, 95 to 100 or 90 to 95%, e.g. about 80, 81, 82, 83, 84, 85, 86, 87, 88, 89, 90, 91, 92, 93, 94, 95, 96, 97, 98, 99 or 100%. The catalyst may be reused for subsequent reactions.

Hydrogenation: an olefin is subjected to a hydrogen atmosphere in the presence of the catalyst. The olefin may be an electron rich olefin. It may be an electron poor olefin. Catalyst may be present at a level of between about 0.1 and about 10 mol % relative to olefin. The catalyst may be present at a level of about 0.1 to 5, 0.1 to 2, 0.1 to 1, 0.1 to 0.5, 0.5 to 10. 1 to 10, 2 to 10, 5 to 10, 0.5 to 5, 0.5 to 2 or 1 to 5 mol %, e.g. about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9 or 10 mol %. The hydrogen pressure may be between about 30 and 150 psi, or between about 30 and 100, 30 and 50, 50 and 150, 100 and 150, 50 and 100 or 80 and 120 psi, e.g. about 30, 40, 50, 60, 70, 80, 90, 100, 110, 120, 130, 140 or 150 psi. It will be understood that the hydrogen may be mixed with an inert gas, for example nitrogen, argon or helium. In this case the pressures described above will represent partial pressures of hydrogen. The olefin may be in solution. The solvent may be incapable of being hydrogenated under the reaction conditions used. The solvent may be for example methanol, ethanol, isopropanol, chloroform, toluene or a combination thereof, or may be some other suitable solvent. The reaction may be conducted at room temperature, or at some other convenient temperature, e.g. between about 15 and about 30° C., or between about 15 and 25, 15 and 20, 20 and 30 or 15 and 25° C., e.g. about 15, 20, 25 or 30° C. The reaction time may be about 1 to 24, 1 to 12, 1 to 6, 1 to 3, 6 to 12, 12 to 18, 18 to 24, 24 to 36, 6 to 36, 12 to 36 or 18 to 36 hours, e.g. about 1, 2, 3, 4, 5, 6, 9, 12, 15, 18, 21, 24, 27, 30, 33 or 36 hours. As described above for the Suzuki reaction, this reaction may also be accelerated by use of microwave irradiation, using the conditions described earlier. Yields from this reaction are typically high. They may be between about 90 and about 100%, or about 90 to 95, 95 to 100, 98 to 100 or 99 to 100%, e.g. about 90, 91, 92, 93, 94, 95, 96, 97, 98, 99, 99.5, 99.6, 99.7, 99.8, 99.9 or 100%. The catalyst may be reused for subsequent reactions.

Reductive amination: an amine and a carbonyl compound are reacted under a hydrogen atmosphere in the presence of the catalyst to generate a substituted amine. The carbonyl compound may be an aldehyde or a ketone. The amine starting material may be an aromatic amine or a heteroaromatic amine or it may be an aliphatic (e.g. linear, branched and/or alicyclic) amine. It may be an aniline. It may be a primary amine. The carbonyl compound may be an alkyl carbonyl compound, e.g. a C1 to C20 straight chain, branched or cyclic aldehyde. The ratio of amine to carbonyl compound may be between about 1:2 and 2:1, or 1:2 and 1:1, 1:1 and 2:1, 1:1.5 and 1.5:1, 1:1.2 and 1.2:1, 1:1.1 and 1.1:1 or 1:1.05 and 1.05:1, e.g. about 1:1, 1:1.01, 1:1.02, 1:1.03, 1:1.04, 1:1.05, 1:1.1, 1:1.15, 1:1.2, 1:1.25, 1:1.3, 1:1.35, 1:1.4, 1:1.45, 1:1.5, 1:1.6, 1:1.7, 1:1.8, 1:1.9, 1:2, 1.01:1, 1.02:1, 1.03:1, 1.04:1, 1.05:1, 1.1:1, 1.15:1, 1.2:1, 1.25:1, 1.3:1, 1.35:1, 1.4:1, 1.45: 1, 1.5:1, 1.6:1, 1.7:1, 1.8:1, 1.9:1 or 2:1. Catalyst may be present at a level of between about 0.1 and about 10 mol % relative to carbonyl compound. The catalyst may be present at a level of about 0.1 to 5, 0.1 to 2, 0.1 to 1, 0.1 to 0.5, 0.5 to 10. 1 to 10, 2 to 10, 5 to 10, 0.5 to 5, 0.5 to 2 or 1 to 5 mol %, e.g. about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9 or 10 mol %. The reaction may be conducted at room temperature, or at some other convenient temperature, e.g. between about 15 and about 30° C., or between about 15 and 25, 15 and 20, 20 and 30 or 15 and 25° C., e.g. about 15, 20, 25 or 30° C. The reaction time may be sufficient to achieve acceptable conversion. The reaction time may be between about 1 and about 12 hours, or about 1 to 6, 1 to 3, 3 to 12, 6 to 12 ore 6 to 9 hours, e.g. about 1, 2, 3, 4, 5, 6, 7, 8, 9, 10, 11 or 12 hours. The hydrogen pressure may be between about 20 and about 60 psi, or about 20 to 40, 40 to 60 or 30 to 50 psi, e.g. about 20, 25, 30, 35, 40, 45, 50, 55 or 60 psi. It will be understood that the hydrogen may be mixed with an inert gas, for example nitrogen, argon or helium. In this case the pressures described above will represent partial pressures of hydrogen. The reaction may be conducted in solution. The solvent may be incapable of being hydrogenated under the reaction conditions used. The solvent may be for example methanol, ethanol, isopropanol, chloroform, toluene or a combination thereof, or may be some other suitable solvent. Yields from this reaction are typically high. They may be between about 90 and about 100%, or about 90 to 95, 95 to 100, 98 to 100 or 99 to 100%, e.g. about 90, 91, 92, 93, 94, 95, 96, 97, 98, 99, 99.5, 99.6, 99.7, 99.8, 99.9 or 100%. The catalyst may be reused for subsequent reactions.

Hydrogenolysis: an epoxide or a diol (e.g. a 1,2- or vicinal diol), and a formate salt, are reacted in the presence of the catalyst to form an alcohol. The formate salt may be an amine formate salt. The amine may be ammonia (whereby the amine salt is ammonium formate) or may be an alkyl, dialkyl or trialkyl ammonium salt. Suitable formate salts include triethylammonium and trimethylammonium formate. The formate salt may be generated in situ or separately, by reaction of formic acid with the amine (or ammonia) in a molar ratio of about 1:1. Catalyst may be present at a level of between about 1 and about 50 mol % relative to carbonyl compound. The catalyst may be present at a level of about 1 to 25, 1 to 10, 1 to 5, 5 to 50, 10 to 50, 25 to 50, 5 to 20 or 5 to 15 mol %, e.g. about 1, 2, 3, 4, 5, 6, 7, 8, 9, 10, 11, 12, 13, 14, 15, 20, 25, 30, 35, 40, 45 or 50 mol %. The reaction may be conducted at room temperature, or at some other convenient temperature, e.g. between about 15 and about 30° C., or between about 15 and 25, 15 and 20, 20 and 30 or 15 and 25° C., e.g. about 15, 20, 25 or 30° C. The ratio of formate salt to carbonyl compound may be between about 2:1 and about 10:1, e.g. about 2:1 to 5:1, 5:1 and 10:1 or 3:1 and 7:1, e.g. about 2:1, 3:1, 4:1, 5:1, 6:1, 7:1, 8:1, 9:1 or 10:1. The reaction may be conducted for sufficient time to achieve a desired conversion. Typical reaction times are between about 1 and about 36 hours. The reaction time may be about 1 to 24, 1 to 12, 1 to 6, 1 to 3, 6 to 12, 12 to 18, 18 to 24, 24 to 36, 6 to 36, 12 to 36 or 18 to 36 hours, e.g. about 1, 2, 3, 4, 5, 6, 9, 12, 15, 18, 21, 24, 27, 30, 33 or 36 hours. As described above for the Suzuki reaction, this reaction may also be accelerated by use of microwave irradiation, using the conditions described earlier. The yield from this reaction is commonly high, and may be between about 80 and about 100%, or about 80 to 95, 80 to 90, 90 to 100, 95 to 100 or 90 to 95%, e.g. about 80, 81, 82, 83, 84, 85, 86, 87, 88, 89, 90, 91, 92, 93, 94, 95, 96, 97, 98, 99 or 100%. The catalyst may be reused for subsequent reactions. The reaction may proceed with retention of configuration of any asymmetric centres in the starting material. The retention of configuration may be between about 80 and about 100%, or about 80 to 95, 80 to 90, 90 to 100, 95 to 100, 99 to 100 or 90 to 95%, e.g. about 80, 81, 82, 83, 84, 85, 86, 87, 88, 89, 90, 91, 92, 93, 94, 95, 96, 97, 98, 99, 99.5, 99.9 or 100%. The catalyst may be reused for subsequent reactions.

The particulate substance of the present invention may be used as a catalyst without loss of catalytic activity, or without substantial loss of activity. It may be conducted such that the loss of activity between subsequent uses of the catalyst is less than about 5%, or less than about 4, 3, 2, 1, 0.5, 0.2 or 0.1% based on yield of product under identical reaction conditions. Thus the particulate substance may be reused as a catalyst in subsequent reaction. It may be reused between 1 and 20 times, or may be reused more than 20 times. It may be reused for example between about 1 and 10, 1 and 5, 5 and 20, and 20 or 5 and 10 times (e.g. 1, 2, 3, 4, 5, 6, 7, 8, 9, 10, 11, 12, 13, 14, 15, 16, 17, 18, 19 or 20 times). Thus the particulate substance used as a catalyst in a particular reaction may be been recycled from a previous reaction. The particulate substance may be used to catalyse a reaction that is regiospecific, stereospecific or both. The retention of stereochemistry may be between about 80 and about 100%, or about 80 to 95, 80 to 90, 90 to 100, 95 to 100, 99 to 100 or 90 to 95%, e.g. about 80, 81, 82, 83, 84, 85, 86, 87, 88, 89, 90, 91, 92, 93, 94, 95, 96, 97, 98, 99, 99.5, 99.9 or 100%. The regiospecificity may be between about 80 and about 100%, or about 80 to 95, 80 to 90, 90 to 100, 95 to 100, 99 to 100 or 90 to 95%, e.g. about 80, 81, 82, 83, 84, 85, 86, 87, 88, 89, 90, 91, 92, 93, 94, 95, 96, 97, 98, 99, 99.5, 99.9 or 100%. The reactions may be conducted with negligible leaching of palladium from the catalyst. The leaching may be less than about 1%, or less than about 0.5, 0.2, 0.1, 0.05, 0.02 or 0.01% for each reaction.

Thus, in summary, the present application describes the synthesis and catalytic applications of supported palladium, in coupling and hydrogenation reactions. The palladium may be in the form of palladium nanoclusters. It describes the preparation and catalytic applications of supported palladium nanoclusters for pharmaceuticals and fine chemicals syntheses and other applications. In examples, urea and thiourea ligands were effectively immobilized onto the surface of siliceous mesocellular foam (MCF) support. Palladium acetate was reduced to palladium upon heating at 60° C., and the nanoclusters obtained were stabilized by the urea or thiourea ligands. The size of nanoclusters was easily controlled by the reaction conditions. This heterogeneous catalyst was successfully applied towards C—C coupling reactions (such as Heck, Suzuki and Sonogashira coupling reactions), and reduction reactions (such as transfer hydrogenation of ketones, hydrogenation of olefins, reductive amination of amines and aldehydes, and hydrogenolysis of epoxides). It was able to catalyze the reactions in green solvents under mild conditions, and could be easily recycled without loss of activity and selectivity.

The MCF-supported Pd nanoclusters demonstrated high catalytic activity. The surface silanol groups of MCF could be uncapped, partially pre-capped or fully capped with trimethylsilyl (TMS) groups to manipulate the catalyst efficiency. In preparing the particulate substance of the present invention, silanol groups on the surface may be at least partially capped, e.g. with TMS groups at a time selected from before, during and after coupling the palladium species to the support. MCF-supported Pd nanoclusters have successfully catalyzed C—C coupling reactions (Suzuki, Sonogashira and Heck coupling reactions) and hydrogenations (transfer hydrogenation, hydrogenation at low pressures using molecular hydrogen, hydrogenolysis, and reductive amination) with excellent activity, selectivity and recyclability. The reactions were also accomplished under environmentally benign phosphine-free conditions in green solvents. They could be accelerated under microwave irradiation, and may in some cases be completed in a short time (5-10 min) with excellent yield. MCF-supported Pd nanoclusters were much more active compared to commercially available polymer- or carbon-supported catalysts due to their non-swelling characteristics, high surface area and ultralarge pore of the MCF support and the stabilization by urea or thiourea ligand.

Polymer-, carbon- or silica-supported and microemulsion-templated Pd catalysts have been reported previously. However, there have not been reports on MCF-supported Pd nanocluster catalysts that demonstrate high catalytic efficiency and excellent recyclability without loss in activity and selectivity.

The inventors consider that MCF-supported Pd species could be applied to any or all types of palladium-catalyzed conversions in organic chemistry. A similar approach for immobilizing metal nanoclusters could also be widely applied towards deriving novel metal oxide (e.g. silica)-supported metal catalysts for the synthesis of a wide variety of fine chemicals and pharmaceuticals, etc. Such novel catalysts could offer high activity, selectivity and stability. They could be easily recycled for reuse, and may be employed in continuous reactions under mild reaction conditions and in green (i.e. environmentally benign) solvents.

BRIEF DESCRIPTION OF THE DRAWINGS

A preferred embodiment of the present invention will now be described, by way of an example only, with reference to the accompanying drawings wherein.

DETAILED DESCRIPTION OF THE PREFERRED EMBODIMENTS

Figure 1:
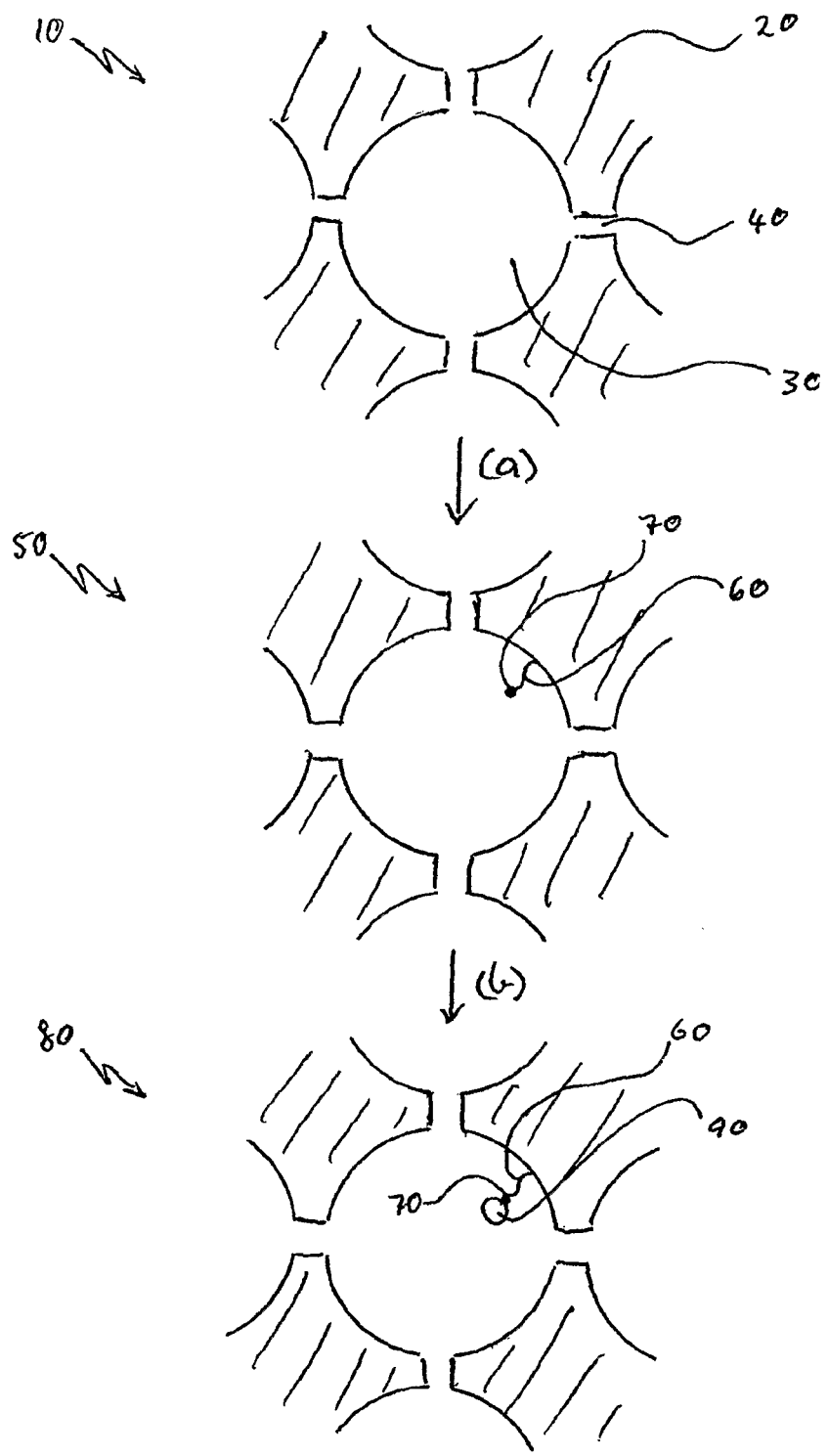
FIG. 1 shows a diagrammatic representation of the production of supported palladium nanoclusters as described in the present invention.

FIG. 1 illustrates the process for making the particulate substance of the present invention. In FIG. 1, structure 10 shows a portion of a particle of mesoporous siliceous foam. Solid matter 20 represents silica, having silanols on the surface thereof. Relatively large pores 30 are connected by relatively small windows 40. Pores 30 are typically about 20 to 50 nm in diameter, and windows 40 are typically about 5 to 10 nm in diameter, although these dimensions may be varied considerably. Step (a) of the process comprises converting the mesoporous siliceous foam to a functionalised support, having partial structure 50, in which the surface of pores 30 have been functionalised by a group comprising a linking group 60 and a binding group 70, e.g. a urea group. Binding group 70 is capable of complexing with or otherwise binding palladium nanoclusters. It will be understood that, whereas in FIG. 1 only a single group is shown, the surface will have many such groups attached, both in the windows and in the pores. They may also be present on the outside surface of the particles. The attachment of these groups can be achieved by reacting with a solution of a suitable functionalising reagent, in which binding group 70 and an attaching group, e.g. a trimethylsilyl group are attached to the linking group. In step (b) of FIG. 1, the functionalised support is converted to the particulate substance 80 of the invention by formation of palladium nanoclusters 90 and complexation or binding thereof to the functionalised support 50. In order to achieve this, a functionalised support 50 is exposed to a solution of a palladium salt, e.g. Pd(OAc)$_2$, and heated so as to reduce the Pd(II) to Pd(0), to form palladium nanoclusters 90. As these form, they complex with binding group 70 so as to form particulate substance 80 having palladium nanoclusters 90 attached to the walls of the pores and windows thereof, and possibly also on the outside surface thereof.

In the present work, palladium was immobilized on siliceous mesocellular foam (MCF) through the use of urea ligands (see Scheme 1).

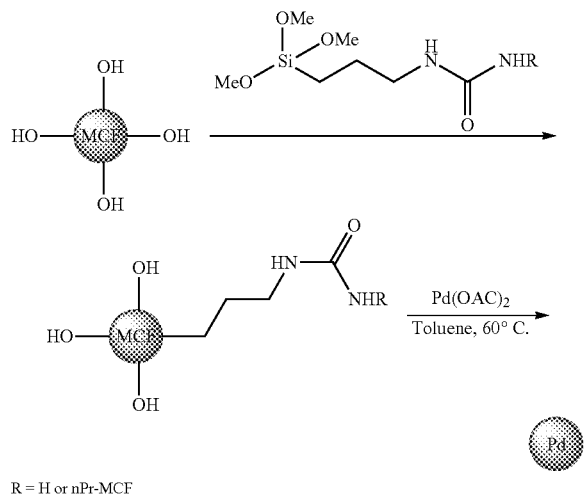

Scheme 1. Immobilization of Pd nanoclusters on Urea-MCF.

R = H or nPr-MCF

MCF was selected as the support since it possessed a 3-dimensional, interconnected pore structure with ultralarge cell-like pores (24-42 nm) that were connected by windows of 9-22 nm. Templated by oil-in-water microemulsions, MCF also has a high surface area of 500-800 m$^2$/g and a high surface concentration of silanols. The urea groups were introduced onto the pore surface of spherical MCF microparticles by reacting (CH$_3$O)$_3$Si(CH$_2$)$_3$NCONH$_2$ or (CH$_3$O)$_3$Si (CH$_2$)$_3$ NHCONH(CH$_2$)$_3$Si(OCH$_3$) with 550° C.-calcined MCF in toluene at 80° C. for 24 h. Loading of the urea ligand in the resulting urea-MCF was determined by elemental analysis to be 1.8 mmol/g. Pd(OAc)$_2$ (1.5 mmol) was dissolved in ethylacetate, and introduced to Urea-MCF (1 g). The mixture was stirred at room temperature for 30 min, and then heated at 60° C. for 24 h. The initially dark brown palladium acetate solution was reduced to elemental palladium, and was deposited onto the MCF support via the urea ligands. The supernatant was clear after the reaction, indicating the complete immobilization of Pd on MCF. The Pd/Urea-MCF was filtered, washed and dried.

Figure 2:
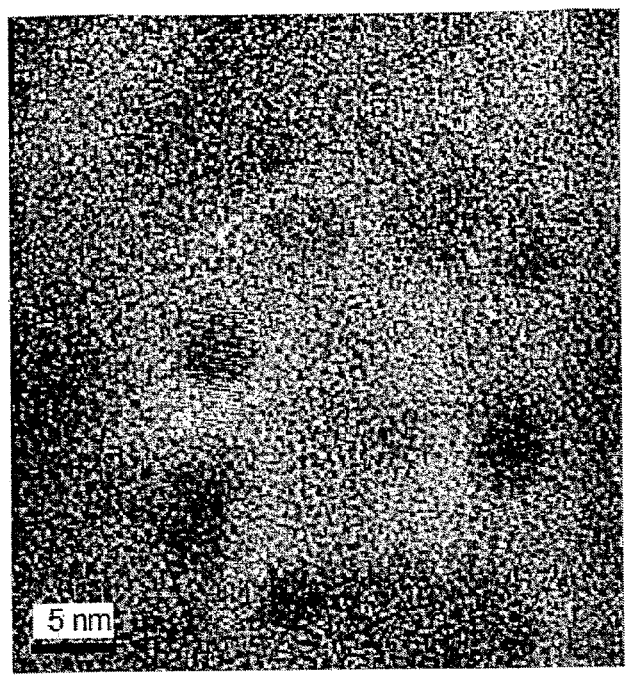
FIG. 2 shows a TEM (transmission electron microscope) micrograph of Pd/Urea-MCF with Pd nanoclusters of 4-6 nm.
Figure 2A:
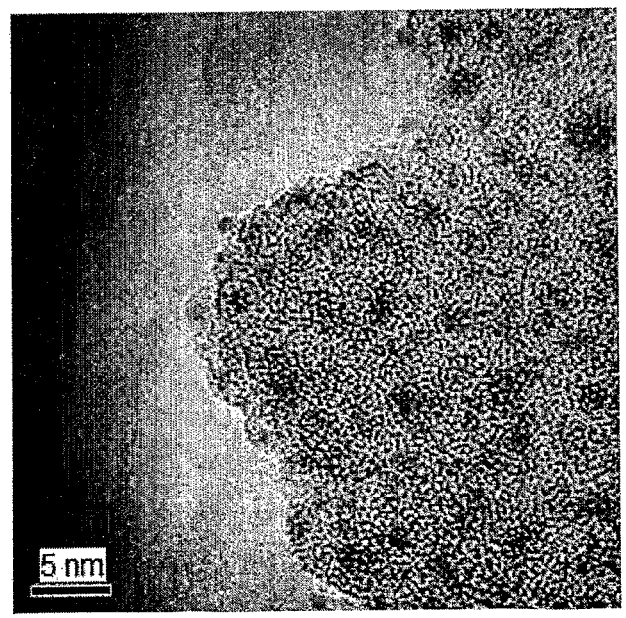
FIG. 2a shows a TEM micrograph of Pd/Urea-MCF with Pd nanoclusters of 2-3 nm.
Figure 3:
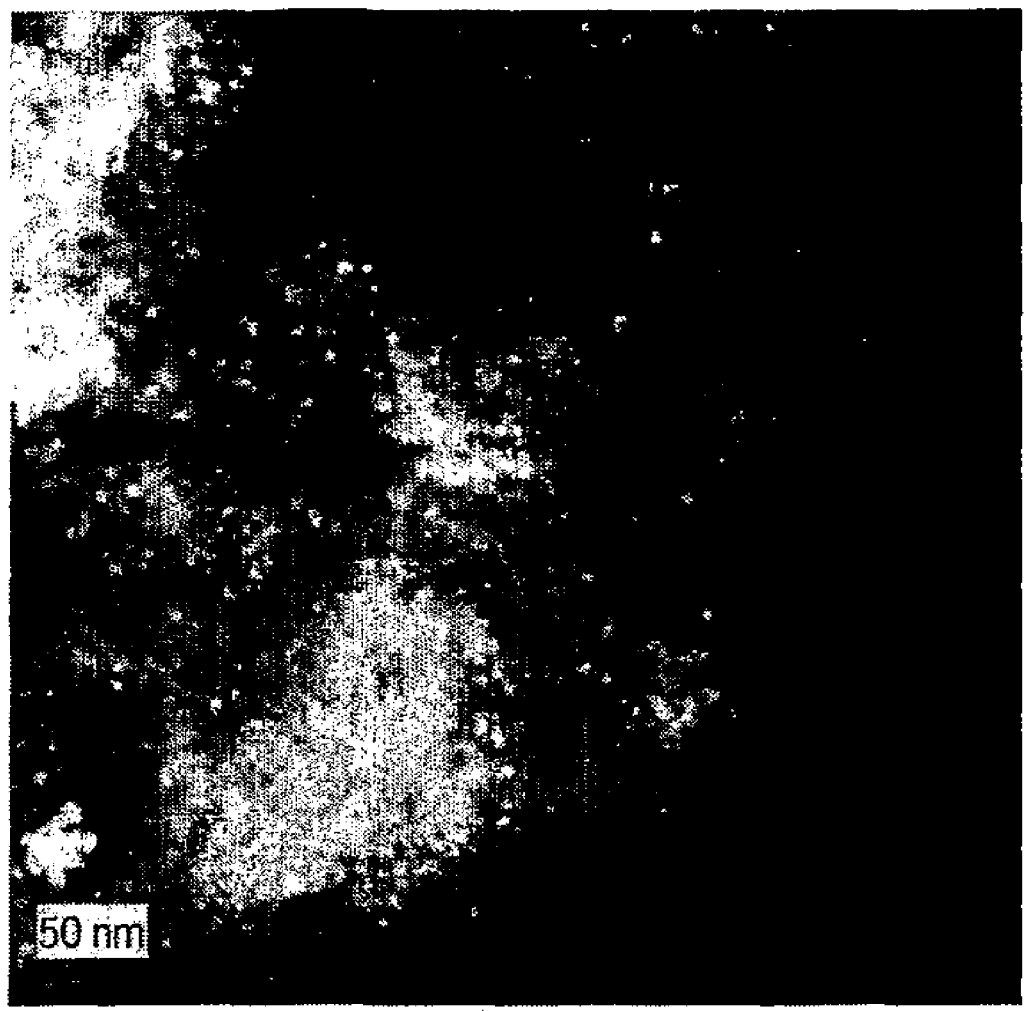
FIG. 3 shows a STEM (scanning transmission electron microscope) micrograph of Pd/Urea-MCF with Pd nanoclusters of 2-3 nm.
Figure 4:
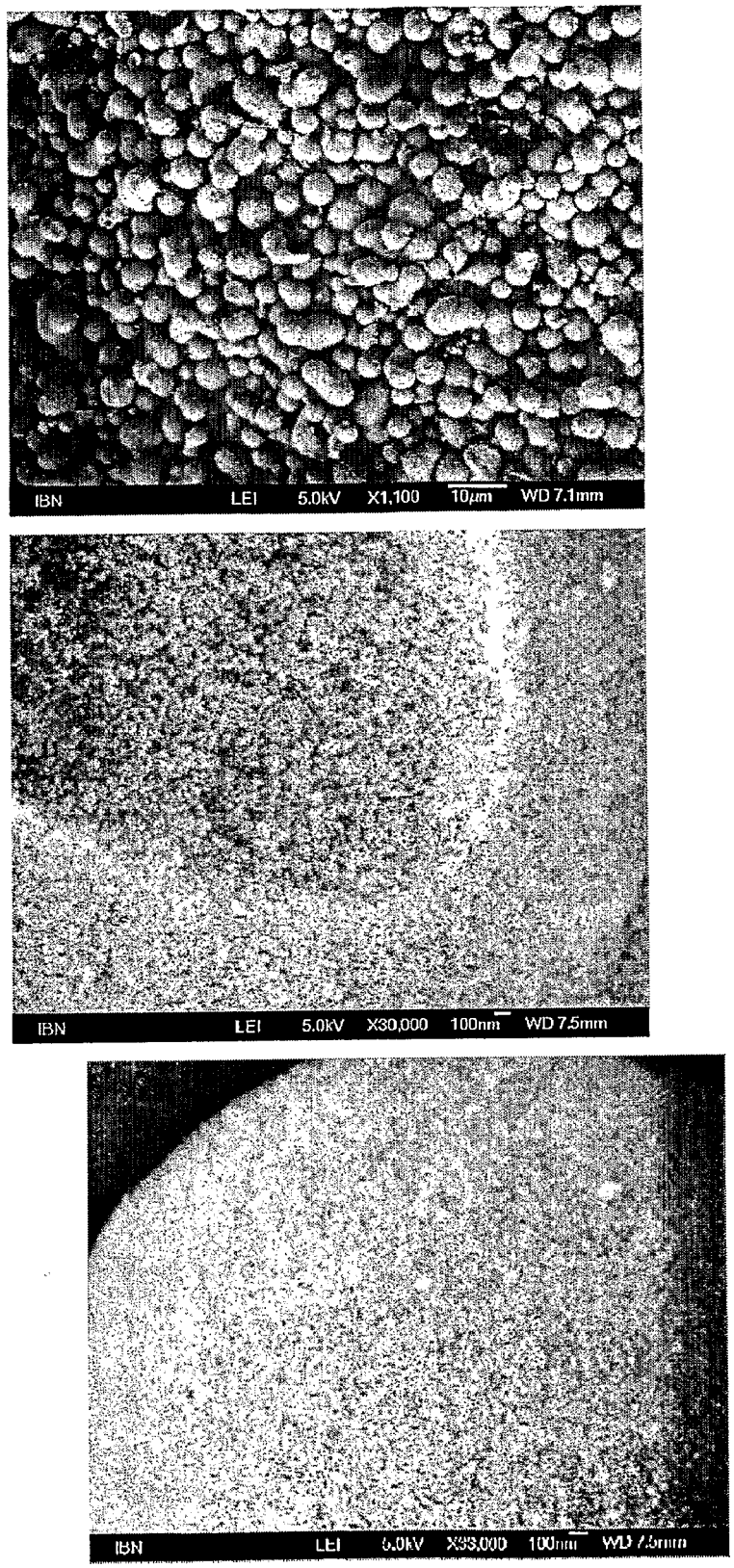
FIG. 4 shows a SEM (scanning electron microscope) micrographs of Pd/Urea-MCF.
Figure 5:
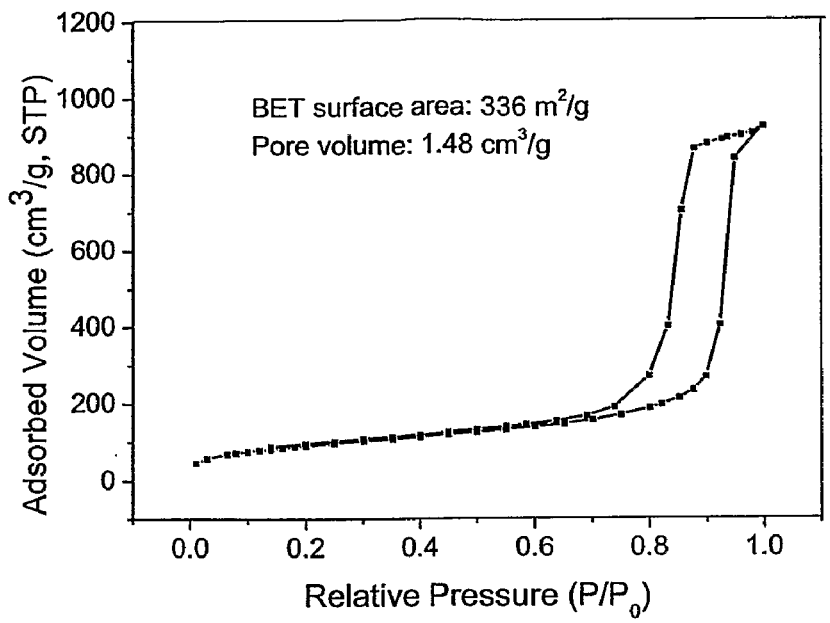
FIG. 5 shows a $N_2$ adsorption-desorption isotherm of Pd/Urea-MCF with Pd nanoclusters of 4-6 nm.
Figure 6:
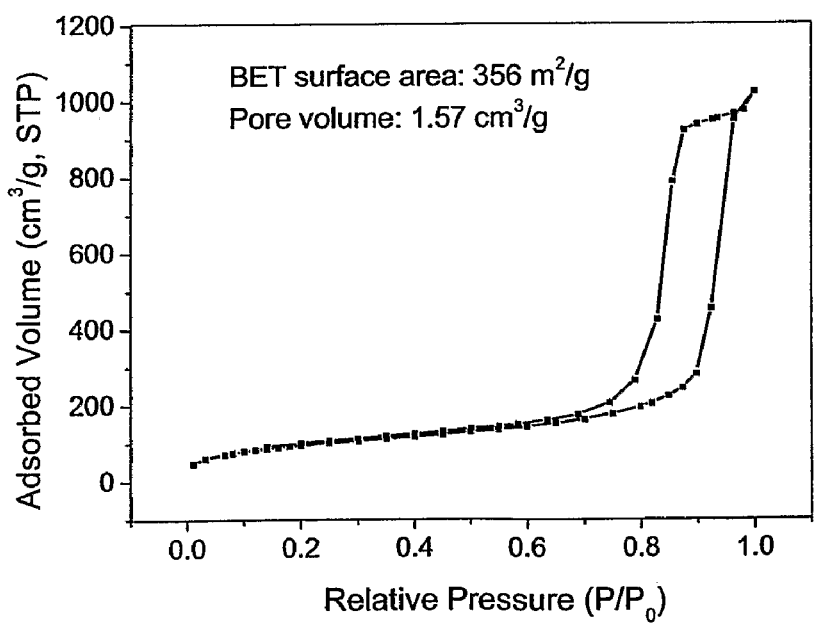
FIG. 6 is a $N_2$ adsorption-desorption isotherm of Pd/Urea-MCF with Pd nanoclusters of 2-3 nm.
Figure 7:
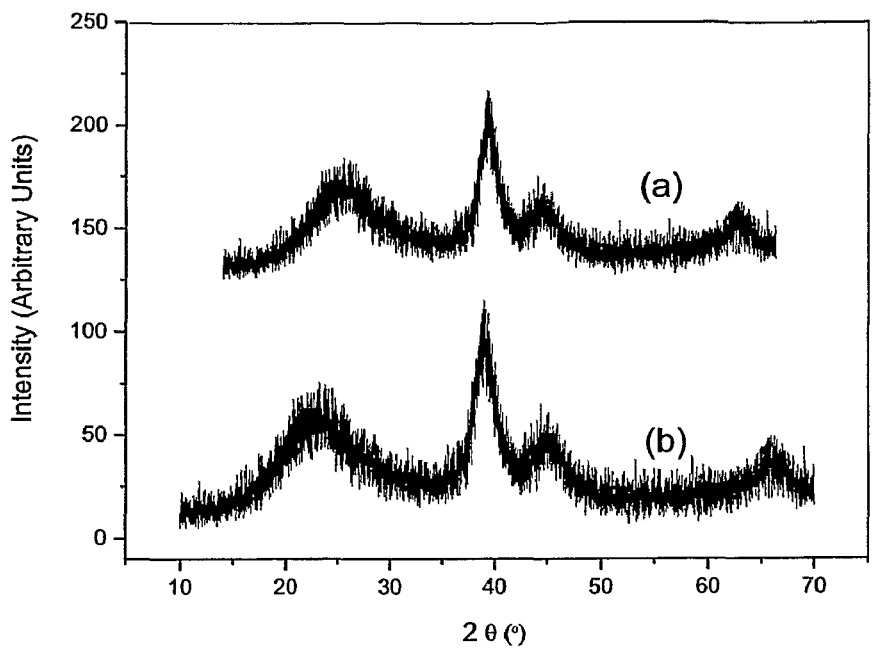
FIG. 7 shows an XRD pattern of Pd/Urea-MCF with Pd nanoclusters of 2-3 nm (a) before and (b) after 10 rims of transfer hydrogenation of acetophenone at room temperature.
Figure 12:
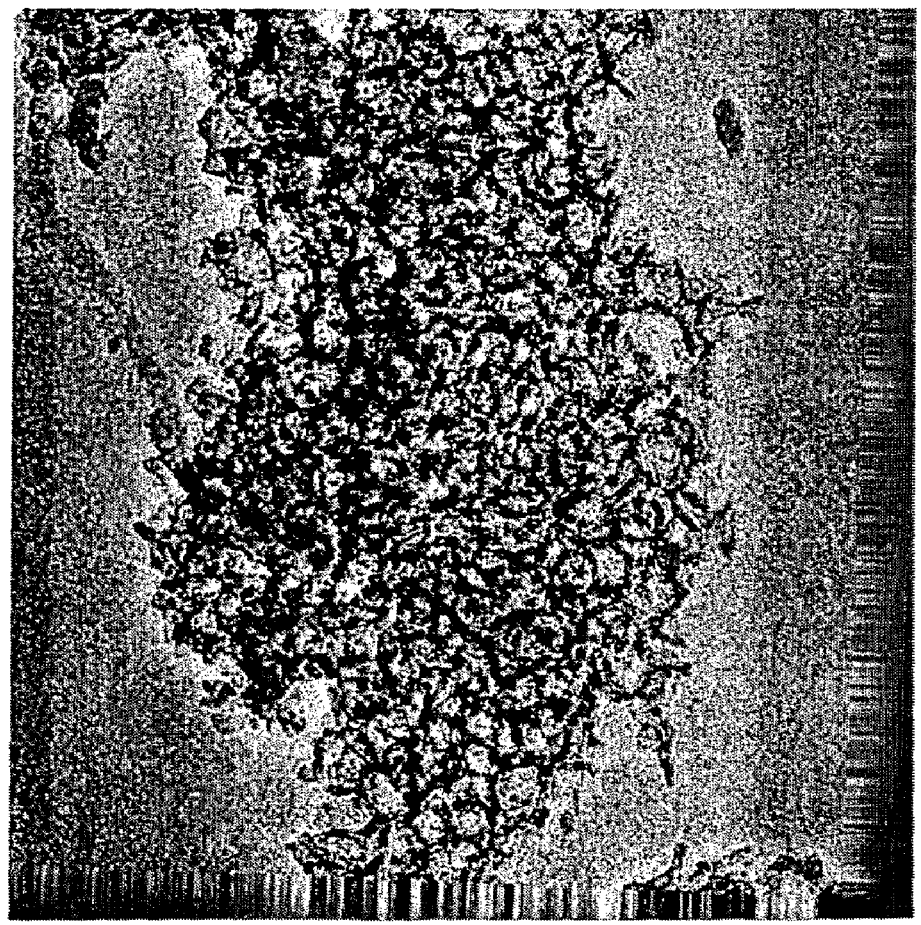
FIG. 12 shows Pd and Si mapping illustrating the high Pd dispersion within the mesopores of the siliceous MCF support.

The Pd nanoclusters deposited on Urea-MCF have a size distribution in the range of 4-6 nm (FIG. 2), and were dispersed uniformly on the support. The size of the nanoclusters could also be controlled by changing the Pd(OAc)$_2$ concentration during the synthesis. For example, when the amount of Pd(OAc)$_2$ was reduced by half, similar procedure would result in the formation of 2-3 nm particles (FIG. 2$a$). Scanning transmission electron microscopy (STEM) (FIG. 3) and Si and Pd mapping by transmission electron microscopy (TEM) (FIG. 12) illustrated the uniformity of the Pd particles dispersed within the mesopores of MCF. Scanning electron microscopy (SEM) (FIG. 4) and nitrogen adsorption-desorption isotherms (FIGS. 5 and 6) illustrated that the uniform, ultralarge pores of the MCF support were retained in the Pd/Urea-MCF catalysts. X-ray diffraction (XRD) studies confirmed the ultrafine grain size (2-3 nm) and high dispersion of Pd nanoclusters in the Pd/Urea-MCF catalyst (FIG. 7($a$)).

Figure 8:
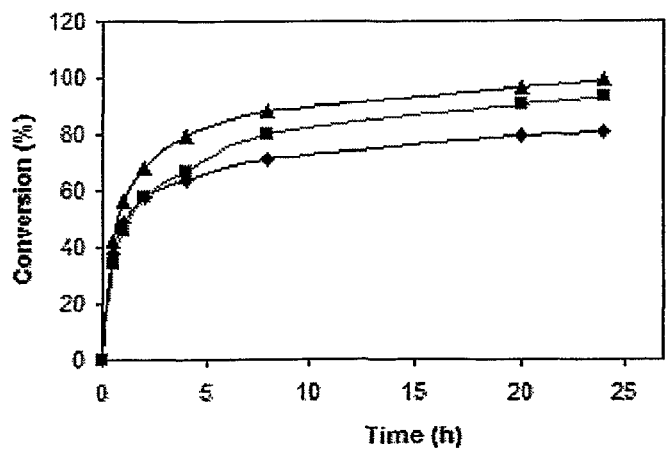
FIG. 8 is a graph illustrating Suzuki coupling of iodobenzene and phenylboronic acid (first run) over (♦) 10% Pd/C, and Pd/Urea-MCF with (▲) 2-3 nm and (■) 4-6 nm Pd nanoclusters.

The catalytic activity of Pd/Urea-MCF was examined for the Suzuki coupling reaction of iodoanisole and phenyl boronic acid in an ethanol/water mixture (9:1 volume ratio), using Na$_2$CO$_3$ as the base (Table 1). After 24 h, the coupling product was isolated in 99% yield (Table 1, Entry 1). Pd/Urea-MCF catalysts with 2-3 nm and 4-6 nm Pd nanoclusters were compared to commercial 10% Pd/C catalyst (Sigma-Aldrich) with 2-3 nm Pd nanoclusters for the Suzuki coupling of iodobenzene and phenylboronic acid. Pd/Urea-MCF with 2-3 nm Pd nanoclusters outperformed the commercial 10% Pd/C catalyst and the Pd/Urea-MCF catalyst with 4-6 nm Pd nanoclusters (FIG. 8). Pd leaching was examined by analyzing the supernatant of the reaction. No Pd was found to have leached from the Urea-MCF support even after 5 days of a blank experiment under similar reaction conditions. The Suzuki reaction proceeded faster when the solvent was changed to a ethanol/water mixture of 1:1 volume ratio at 80° C. (Table 1, Entry 6), giving a 98% yield in 6 h instead of 24 h under the typical homogeneous reaction conditions.

TABLE 1

Suzuki Coupling of Aryl Halides with Aryl Boronic Acids[a]

| entry | aryl halide | aryl boronic acid | product | time (h) | yield (%) |
|---|---|---|---|---|---|
| 1 | I-C$_6$H$_5$ | B(OH)$_2$-C$_6$H$_5$ | biphenyl | 6<br>0.167[c] | 99<br>99[c] |

TABLE 1-continued

Suzuki Coupling of Aryl Halides with Aryl Boronic Acids[a]

| entry | aryl halide | aryl boronic acid | product | time (h) | yield (%) |
|---|---|---|---|---|---|
| 2 | Ph-Br | Ph-B(OH)$_2$ | biphenyl | 12 | 89 |
| 3 | 4-MeO-C$_6$H$_4$-Br | Ph-B(OH)$_2$ | 4-methoxybiphenyl | 12 | 97 |
| 4 | 4-O$_2$N-C$_6$H$_4$-Br | Ph-B(OH)$_2$ | 4-nitrobiphenyl | 12 | 94 |
| 5 | 4-F-C$_6$H$_4$-Br | 4-MeO-C$_6$H$_4$-B(OH)$_2$ | 4-fluoro-4'-methoxybiphenyl | 12 | 91 |
| 6[d] | Ph-I | 4-MeO-C$_6$H$_4$-B(OH)$_2$ | 4-methoxybiphenyl | 12<br>6[e] | 99<br>98 |
| 7 | Ph-Br | 4-MeO-C$_6$H$_4$-B(OH)$_2$ | 4-methoxybiphenyl | 20 | 98 |
| 8 | 4-MeO-C$_6$H$_4$-Br | 4-MeO-C$_6$H$_4$-B(OH)$_2$ | 4,4'-dimethoxybiphenyl | 12 | 92 |

[a]Reaction conditions: 1 mol % Pd/Urea-MCF catalyst with Pd nanoclusters of 2-3 nm, 1 mmol of aryl halide, 1.25 mmol of aryl boronic acid, 1.5 mmol of sodium carbonate, 5 ml of ethanol/water mixture (volume ratio = 9:1), 80° C., argon atmosphere.
[b]Isolated yield.
[c]Under microwave conditions.
[d]Recycled 5 times without any loss in the product yield.
[e]Volume ratio of ethanol/water mixture used 1:1.

Pd/Urea-MCF catalyst also provided excellent yields for the Heck coupling of iodoarenes (Table 2). It was recycled without any significant loss in activity and selectivity

TABLE 2

Heck Coupling of Aryl Halides and Alkenes[a]

| entry | aryl halide | alkene | product | time (h) | yield (%)[b] |
|---|---|---|---|---|---|
| 1 | 4-NO₂-C₆H₄-I | CH₂=CH-COOnBu | 4-O₂N-C₆H₄-CH=CH-COOnBu | 18 | 96 |
| 2 | 4-NO₂-C₆H₄-Br | CH₂=CH-COOnBu | 4-O₂N-C₆H₄-CH=CH-COOnBu | 24 | 92 |
| 3 | 4-MeO-C₆H₄-I | CH₂=CH-COOnBu | 4-MeO-C₆H₄-CH=CH-COOnBu | 18 | 95 |
| 4 | 4-MeO-C₆H₄-Br | CH₂=CH-COOnBu | 4-MeO-C₆H₄-CH=CH-COOnBu | 24 | 89 |
| 5[c] | C₆H₅-I | CH₂=CH-COOnBu | C₆H₅-CH=CH-COOnBu | 20 | 92 |
| 6 | C₆H₅-Br | CH₂=CH-COOnBu | C₆H₅-CH=CH-COOnBu | 24 | 88 |
| 7 | C₆H₅-I | CH₂=CH-COOtBu | C₆H₅-CH=CH-COOtBu | 20 | 93 |

TABLE 2-continued

Heck Coupling of Aryl Halides and Alkenes[a]

| entry | aryl halide | alkene | product | time (h) | yield (%)[b] |
|---|---|---|---|---|---|
| 8 | PhBr | CH2=CH-COOtBu | Ph-CH=CH-COOtBu | 24 | 84 |

[a]Reaction conditions: 1 mol % Pd/Urea-MCF catalyst with Pd nanoclusters of 2-3 nm, 1 mmol of aryl halide, 1.25 mmol of olefin, 2 mmol of triethylamine, 5 ml of toluene, 100° C., argon atmosphere.
[b]Isolated yield.
[c]Recycled 5 times without loss in activity and selectivity.

Figure 9:
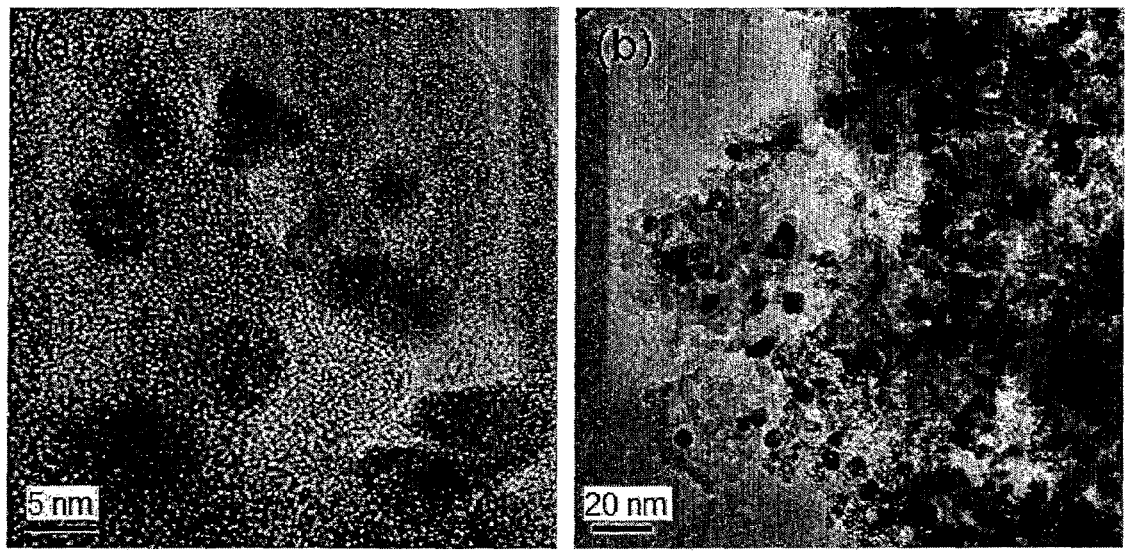
FIG. 9 shows a TEM micrograph of Pd/Urea-MCF with Pd nanoclusters of (a) 4-6 nm and (b) 2-4 nm after 10 runs of transfer hydrogenation of acetophenone at room temperature.
Figure 10:
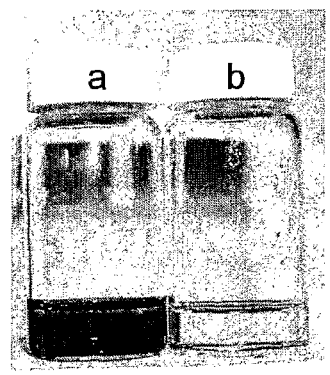
FIG. 10 shows photographs of filtrates of transfer hydrogenation of acetophenone over (a) 10% Pd/C and (b) 10 mol % of 5% Pd/Urea-MCF with 2-3 nm Pd nanoclusters: the brown colour in (a) indicates significant Pd leaching from 10% Pd/C. ICP-MS analysis shows almost 90% of the Pd loaded was leached from 10% Pd/C in the first run, whereas only a total of 1.25% of the Pd loaded was leached from 5% Pd/Urea-MCF after 10 runs.

Excellent yields were achieved for the transfer hydrogenation of various ketones over Pd/Urea-MCF. Typically, transfer hydrogenation of ketones was carried out using 10 mol % of the 5% Pd/Urea-MCF catalyst and 5 equiv of formic acid/triethylamine mixture as the hydrogen source in ethylacetate at room temperature. The heterogeneous catalyst was easily recovered and reused several times without any loss in reactivity and selectivity (Table 3). After 10 runs of transfer hydrogenation of acetophenone (Table 3, Entry 1), the Pd nanoclusters remained highly dispersed on Urea-MCF (FIG. 9), and the catalyst demonstrated negligible loss in activity. The X-ray diffraction (XRD) pattern of Pd/Urea-MCF consisted of Pd(0) peaks. Peak broadening analysis by Scherrer's method indicated the average palladium crystallite size grew slightly from 2-3 mm (FIG. 7(a)) to 4-5 nm after 10 runs (FIG. 7(b)). FIG. 10(b) shows the filtrate of the reaction system to be clear; ICP-MS confirmed that only a total of 1.25% of the Pd loaded in 5% Pd/Urea-MCF was leached after 10 runs. In contrast, the filtrate of the reaction system containing 10% Pd/C was brown in color FIG. 10(a), due to almost 90% leaching of the Pd loaded after just 1 run. Interestingly, when the transfer hydrogenation of various ketones was performed in water at 60° C. with ammonium formate as the hydrogen source instead of formic acid/triethylamine mixture, the reaction was completed more quickly (i.e. in 2 h instead of 24 h), giving an excellent yield of the corresponding alcohol.

TABLE 3

Transfer Hydrogenation of Ketones[a]

| entry | ketone | product | time (h) | yield (%)[b] |
|---|---|---|---|---|
| 1[c] | acetophenone | 1-phenylethanol | 24<br>0.25[d]<br>2[e] | 87<br>85<br>82 |
| 2 | 4'-bromoacetophenone | 1-(4-bromophenyl)ethanol | 24<br>2[e] | 88<br>84 |
| 3 | 4'-chloroacetophenone | 1-(4-chlorophenyl)ethanol | 24 | 88 |
| 4 | propiophenone | 1-phenyl-1-propanol | 24<br>2[e] | 84<br>80 |

TABLE 3-continued

Transfer Hydrogenation of Ketones[a]

| entry | ketone | product | time (h) | yield (%)[b] |
|---|---|---|---|---|
| 5 | PhC(O)CH₂C(O)OMe | PhCH(OH)CH₂C(O)OMe | 18 | 96 |
| 6[c] | PhCH=CHC(O)CH₃ | PhCH=CHCH(OH)CH₃ | 18 | 99 |
| 7 | 2-acetylnaphthalene | 1-(2-naphthyl)ethanol | 24<br>2[e] | 92<br>94 |
| 8 | PhC(O)CF₃ | PhCH(OH)CF₃ | 48 | 99 |
| 9 | PhCH₂CH₂C(O)CH₃ | PhCH₂CH₂CH(OH)CH₃ | 24 | 95 |
| 10[c] | acetylferrocene | 1-ferrocenylethanol | 12 | 99 |
| 11 | 1,1'-diacetylferrocene | 1,1'-bis(1-hydroxyethyl)ferrocene | 12 | 99 |
| 12 | 2-acetylpyridine | 1-(2-pyridyl)ethanol | 15 | 99 |

[a]Reaction conditions: 10 mol % of 5% Pd/Urea-MCF catalyst with Pd nanoclusters of 2-3 nm, 1 mmol of ketone, 5 mmol of formic acid:triethylamine (1:1), 5 ml of ethylacetate, 25° C.
[b]Isolated yield.
[c]Recycled 10 times without any loss in activity and selectivity.
[d]Under microwave conditions.
[e]Used ammoniumformate as hydrogen source and water as solvent at 60° C.

Pd/Urea-MCF was also examined for the hydrogenation of activated olefins (Table 4) such as dimethylitaconate (Table 4, entry 1) under low pressure (3 atm). The hydrogenated product, 1-methyl-dimethylsuccinate, was obtained in 99.9% yield, and the catalyst was successfully recycled and reused without any loss in activity for 10 runs. Hydrogenation also proceeded with excellent yield and catalyst recyclability for a variety of olefins (Table 4).

Next, the catalytic activity of Pd/Urea-MCF for the reductive amination of aldehydes and amines was examined. This reaction is very important for producing secondary amines in the pharmaceuticals and specialty chemicals industry. Excellent conversions and yields of the corresponding amines were achieved under mild conditions, and the catalyst was recycled 10 times without any significant loss in reactivity and selectivity (Table 5).

TABLE 4

Hydrogenation of Olefins[a]

| entry | olefin | product | time (h) | yield (%)[b] |
|---|---|---|---|---|
| 1[c] | MeO-C(=O)-C(=CH2)-CH2-C(=O)-OMe | MeO-C(=O)-CH(CH3)-CH2-C(=O)-OMe | 6 | 99.9 |
| 2 | EtO-C(=O)-C(=CH2)-CH2-C(=O)-OEt | EtO-C(=O)-CH(CH3)-CH2-C(=O)-OEt | 6 | 99.9 |
| 3 | naphthyl-CH=C(NHAc)-C(=O)-OMe | naphthyl-CH2-CH(NHAc)-C(=O)-OMe | 6 | 99.9 |
| 4 | (MeO,AcO-phenyl)-CH=C(NHAc)-C(=O)-OMe | (MeO,AcO-phenyl)-CH2-CH(NHAc)-C(=O)-OMe | 6 | 99.9 |
| 5 | Ph-CH=CH-C(=O)-CH3 | Ph-CH2-CH2-C(=O)-CH3 | 8 | 99.9 |
| 6[c] | Ph-CH=CH-C(=O)-OMe | Ph-CH2-CH2-C(=O)-OMe | 8 | 99.9 |
| 7 | 4-Br-C6H4-CH=CH2 | 4-Br-C6H4-CH2-CH3 | 18 | 99 |
| 8 | Ph-CH2-O-CH2-CH=CH2 | Ph-CH2-O-CH2-CH2-CH3 | 18 | 99 |

[a]Reaction conditions: 1 mol % Pd/Urea-MCF catalyst with Pd nanoclusters of 2-3 nm, 1 mmol of olefin, 40 psi or 100 psi of hydrogen (for entries 1-6 and 7-8, respectively), 5 ml of methanol/ethanol, 25° C.
[b]Isolated yield.
[c]Recycled 10 times without any loss in product yield.

TABLE 5

Reductive Amination of Aldehydes[a]

| entry | amine | aldehyde | product | time (h) | yield (%) |
|---|---|---|---|---|---|
| 1[c] | 4-methoxyaniline | isovaleraldehyde | N-(3-methylbutyl)-4-methoxyaniline | 6 | 99.9 |
| 2[c] | 4-methoxyaniline | valeraldehyde | N-pentyl-4-methoxyaniline | 8 | 99.9 |
| 3 | aniline | isovaleraldehyde | N-(3-methylbutyl)aniline | 6 | 99.9 |
| 4 | aniline | valeraldehyde | N-pentylaniline | 8 | 99.9 |
| 5 | 4-bromoaniline | isovaleraldehyde | N-(3-methylbutyl)-4-bromoaniline | 6 | 99.9 |
| 6 | 4-bromoaniline | valeraldehyde | N-pentyl-4-bromoaniline | 8 | 99.9 |

[a]Reaction conditions: 1 mol % Pd/Urea-MCF catalyst with Pd nanoclusters of 2-3 nm, 1.01 mmol of aniline, 1.0 mmol of aldehyde, 40 psi of hydrogen, 5 ml of methanol, 25° C.
[b]Gas chromatography (GC) yield.
[c]Recycled 10 times without any loss in activity and selectivity.

The reductive ring opening of epoxides to the corresponding alcohols has emerged as a powerful tool in organic synthesis. It is of great interest to develop a practical, economical, and environmentally friendly process for this reaction. The efficiency and stability of Pd/Urea-MCF catalyst was examined with trans-stilbene oxide as a substrate (Table 6, Entry 4). Notably, the hydrogenolysis reaction reached completion with excellent yields in 10 successive runs. The catalyst could be recovered by simple filtration, and be reused without loss of activity. A variety of benzylic epoxides were then subjected to the same hydrogenolysis conditions, and good yields of homobenzylic alcohols were obtained consistently. To further extend the scope of this catalytic system, we turned our attention to the hydrogenolysis of chiral epoxides, which is used for the synthesis of anti-inflamatory arylpropionic acids. Hydrogenolysis of chiral alpha-methylstyrene oxide generated the corresponding terminal alcohol with the retention of configuration in excellent yield (Table 6, Entry 8).

TABLE 6

Hydrogenolysis of Epoxides and Diols[a]

| entry | epoxide/diol | hydrogen source | time (h) | yield (%)[b] |
|---|---|---|---|---|
| 1 | | | 12 | 91 |
| 2 | | | 12 | 94 |
| 3 | | | 12 | 97 |
| 4[c] | | | 24 | 99 |
| 5 | | | 24 | 94 |
| 6 | | | 24 | 98 |
| 7 | | | 24 | 86 |
| 8[d] | | | 12 | 98 |
| 9 | | | 12 | 88 |

TABLE 6-continued

Hydrogenolysis of Epoxides and Diols[a]

| entry | epoxide/diol | hydrogen source | time (h) | yield (%)[b] |
|---|---|---|---|---|
| 10 | Ph-C(OH)(CH₃)-CH₂OH (2-phenyl-1,2-propanediol) | Ph-CH(CH₃)-CH₂OH (2-phenyl-1-propanol) | 12 | 94 |

[a]Reaction conditions: 10 mol % Pd/Urea-MCF catalyst with Pd nanoclusters of 2-3 nm, 1 mmol of epoxide or diol, 5 mmol of ammonium formate, 5 ml of ethylacetate, 25° C.
[b]Isolated yields.
[c]Recycled 10 times without any loss in reactivity and selectivity.
[d]Retention of configuration.

Figure 11:
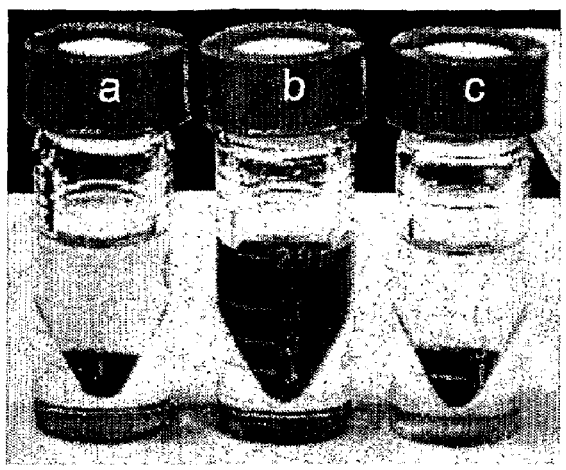
FIG. 11 shows photographs of reaction mixtures from (a) heterogeneous transfer hydrogenation of acetophenone, and (b) homogeneous and (c) heterogeneous Suzuki coupling of iodobenzene with phenylboronic acid.

In the case of transfer hydrogenation, hydrogenation, hydrogenolysis and reductive amination, the total Pd leached after 10 recycles was determined by inductively coupled plasma mass spectrometry (ICP-MS) to be <1.5% of the total Pd loaded in the catalyst. In the case of Heck and Suzuki coupling reactions, the total Pd leached after 5 recycles was <5% as determined by ICP-MS. FIG. 11 illustrate that the supernatant of the heterogeneous reaction systems containing Pd/Urea-MCF was very clear. Negligible leaching of Pd was observed, and this novel catalyst could be easily isolated and recycled.

Pd/Urea-MCF was found to provide even faster reaction rates for coupling reactions and transfer hydrogenations with the aid of microwave. Excellent conversions were achieved under low frequency and short reaction time. For example, 99% conversion was attained in 10 min in the Suzuki coupling of iodobenzene and phenylboronic acid (Table 1, Entry 1). 85% yield of the corresponding alcohol was achieved in 15 min for the transfer hydrogenation of acetophenone under microwave (Table 3, Entry 1). In contrast, 87% yield would be obtained in 24 h under normal reaction conditions at room temperature.

In conclusion, active Pd nanoclusters could be easily prepared with high yields on urea-modified MCF. They were formed by the reduction of Pd(OAc)$_2$, and were stabilized by the urea ligands on the MCF surface. The ultralarge pores of MCF facilitated reactions involving bulky substrates. The resulting Pd/Urea-MCF catalyst demonstrated excellent activity for transfer hydrogenation, hydrogenation and C—C coupling reactions, and were superior to commercially available 10% Pd/C or polymer-supported Pd-Encat. The facile synthesis and novel design for supported metal catalyst described herein might be widely applied to derive metallic nanoclusters supported on modified MCF for a wide variety of catalytic reactions in chemical syntheses. We are currently examining other Pd-catalyzed reactions, and immobilizing other metals (e.g. Rh, Ru, Cu, Ir and In) on MCF for various catalytic applications.

Experimental Section

All chemicals were purchased from Aldrich, and used as received without further purification. $^1$H and $^{13}$C nuclear magnetic resonance (NMR) spectroscopy (Bruker 400 MHz Spectrometer), Fourier-transform infrared (FTIR) spectroscopy (Digilab FTS7000 FTIR spectrometer equipped with MTEC 300 photoacoustic detector), XRD (Philips) XPert PRO X-ray diffraction system), $N_2$ adsorption-desorption analysis (Micromeritics ASAP 2020M system), elemental analysis (Exeter Analytical CE440 CHN analyzer), transmission electron microscopy (TEM) and scanning transmission electron microscopy (STEM) (FEI Tecnai G20, 200 kV), scanning electron microscopy (SEM) (JEOL JSM-6700F) and ICP-MS (Elan DRCII, PerkinElmer SCIEX) were performed for catalyst characterization. Products from catalytic reactions were analyzed by GC (Agilent 6890N).

Synthesis of Urea-MCF

Spherical MCF microparticles (1 g) synthesized according to the method reported[14] were dried for 24 h at 100° C., and cooled to room temperature under argon. Dry toluene (20 ml) was added to the MCF. Next, a solution of trimethoxysilylpropyl urea (2.2 mmol) in toluene (2 ml) was introduced. The mixture was stirred under argon for 10 min, and then heated at 80° C. for 24 h. It was cooled to room temperature, filtered, and washed several times with toluene, ethanol, acetone and dichloromethane to remove any unreacted precursor. The resulting material was suspended in ethanol, and heated at 60° C. overnight, filtered, washed and dried. Elemental analysis showed a loading of 1.80 mmol of urea per gram of MCF.

Synthesis of Pd/Urea-MCF

Urea-MCF (1 g) was suspended in dry toluene (20 ml), and a solution of palladium acetate (1.10 or 0.55 mmol depending on the requirement) in $CH_2Cl_2$ (2 ml) was added dropwise. The mixture was heated at 60° C. until the supernatant became colorless under argon (24 h). It was then cooled to room temperature, filtered, washed and dried to obtain a dark brownish black solid, Pd/Urea-MCF. Elemental analysis showed 1.01 mmol or 0.55 mmol Pd loading per gram of Urea-MCF, corresponding to 5 wt % Pd/Urea-MCF and 10 wt % Pd/Urea-MCF.

General Procedure for Suzuki Coupling Reaction

An oven-dried reaction vial was charged with aryl halide (1 mmol), aryl boronic acid (1.25 mmol), sodium carbonate (1.5 mmol), catalyst (1 mol %), ethanol (4.5 ml) and water (0.5 ml) under argon. The resulting reaction mixture was stirred at room temperature for 10 min, and then heated at 80° C. for a desired period. The reaction was monitored by GC. After completion of the reaction, the mixture was cooled to room temperature, and was filtered through a sintered glass funnel, washed with water (5×5 ml) and ethanol (5×5 ml), and dried under vacuum. The catalyst was recycled 5 times.

General Procedure for Heck Coupling Reaction

An oven-dried reaction vial was charged with aryl halide (1 mmol), olefin (1.25 mmol), triethylamine (2 mmol), catalyst (1 mol %), and toluene (5 ml) under argon. The resulting reaction mixture was stirred at room temperature for 10 min, and then heated at 100° C. for a desired period. The reaction was monitored by GC. After completion of the reaction, the mixture was cooled to room temperature, and was filtered through a sintered glass funnel, washed with toluene (5×5 ml), and dried under vacuum. The catalyst was recycled 5 times.

General Procedure for Transfer Hydrogenation of Ketones

An oven-dried reaction vial was charged with ketone (1 mmol), formic acid/triethylamine mixture (1:1) or ammonium formate (5 mmol), catalyst (10 mol % of 5% Pd/Urea-MCF) and ethylacetate or water (5 ml) under argon. The resulting reaction mixture was stirred at room temperature for 24 h, and the progress of the reaction was monitored by GC. After completion of the reaction, the mixture was filtered through a sintered glass funnel, washed with ethylacetate (5×5 ml), and dried under vacuum. The catalyst was recycled 10 times.

General Procedure for Hydrogenation of Olefins

An oven-dried reaction vial was charged with olefin (1 mmol), catalyst (1 mol %) and methanol/ethanol (5 ml) under argon. The resulting reaction mixture was pressurized with 40-100 psi of hydrogen, and was stirred at room temperature for 6 h. The progress of the reaction was monitored by GC. After completion of the reaction, the mixture was filtered through a sintered glass funnel, washed with methanol (5×5 ml), and dried under vacuum. The catalyst was recycled 10 times.

General Procedure for Reductive Amination of Aldehydes Under Hydrogen

An oven-dried reaction vial was charged with aldehyde (1.0 mmol), primary amine (1.01 mmol), catalyst (1 mol %) and methanol (5 ml) under argon. The resulting reaction mixture was pressurized with 40 psi of hydrogen, and was stirred at room temperature for 6 h. The progress of the reaction was monitored by GC. After completion of the reaction, the mixture was filtered through a sintered glass funnel, washed with methanol (5×5 ml), and dried under vacuum. The catalyst was recycled 10 times.

General Procedure for Hydrogenolysis of Epoxides and Diols

An oven-dried reaction vial was charged with epoxide or diol (1 mmol), ammonium formate (5 mmol), catalyst (10 mol %) and ethylacetate (5 ml) under argon. The resulting reaction mixture was stirred at room temperature for 24 h, and the progress of the reaction was monitored by GC. After completion of the reaction, the mixture was filtered through a sintered glass funnel, washed with ethylacetate (5×5 ml), and dried under vacuum. The catalyst was recycled 10 times.

The invention claimed is:

1. A particulate substance comprising a particulate porous support coupled to a palladium species, wherein the porous support is coupled to the palladium species by a coupling group comprising a linking group and a binding group, said binding group being coupled to the palladium species, wherein the binding group does not contain a thiol group, and wherein the binding group is a urea group or a thiourea group.

2. The particulate substance of claim 1 wherein the palladium species comprises palladium nanoclusters.

3. The particulate substance of claim 1 wherein the porous support is a metal oxide support.

4. The particulate substance of claim 3 wherein the metal oxide is silica.

5. The particulate substance claim 1 wherein the porous support is mesoporous.

6. The particulate substance of claim 1 having a structure in which pores are connected by windows.

7. The particulate substance of claim 6 in which the pores have a mean diameter of between about 5 and about 100 nm, and the windows have a mean diameter of between about 2 and about 50 nm.

8. The particulate substance of claim 1 wherein the porous support is mesoporous siliceous foam.

9. The particulate substance of claim 1 wherein the palladium species comprises palladium nanoclusters and said nanoclusters have a mean diameter between about 1 and about 10 nm.

10. The particulate substance of claim 1 having a mean particle size of between about 1 and about 100 microns.

11. The particulate substance of claim 1 having a palladium loading of between about 0.1 and 2 mmol palladium per gram of support.

12. A process for making a particulate substance of claim 1, said process comprising:
exposing a functionalised particulate porous support to a solution of a palladium salt, said functionalised particulate porous support comprising binding groups capable of binding the palladium species, wherein the binding group is a urea group or a thiourea group; and
converting the palladium salt to the palladium species so as to generate the particulate substance.

13. The process of claim 12 additionally comprising reacting a particulate porous support to a functionalising reagent to form the functionalised particulate porous support, said functionalising reagent comprising the binding group and an attaching group capable of attaching to the particulate porous support.

14. The process of claim 12 wherein the functionalised particulate porous support comprises mesoporous siliceous foam.

15. A method for conducting a reaction comprising exposing one or more reagents to a particulate substance of claim 1, wherein the reaction is selected from the group consisting of:
a Suzuki coupling reaction using an aryl halide and an aryl boronic acid;
a Heck coupling reaction using an aryl halide or an aryl triflate and an olefin;
a hydrogenation reaction using a carbonyl compound or an olefin;
a reductive amination reaction using a carbonyl compound, a primary amine and hydrogen gas; and
a hydrogenolysis reaction using an epoxide or a diol and a formate salt.

16. The particulate substance of claim 1 wherein the palladium species comprises palladium atoms or palladium clusters or both.

* * * * *